US006235711B1

(12) United States Patent
Dutta

(10) Patent No.: US 6,235,711 B1
(45) Date of Patent: *May 22, 2001

(54) CELL ADHESION IHIBITING COMPOUNDS

(75) Inventor: Anand Swaroop Dutta, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,831

(22) Filed: Dec. 21, 1998

(30) Foreign Application Priority Data

Jun. 21, 1996 (GB) .................................................. 9613112

(51) Int. Cl.$^7$ .................................................. A61K 38/12
(52) U.S. Cl. .............................. 514/11; 514/16; 514/17; 514/863; 530/317; 530/328; 530/329; 530/333
(58) Field of Search ................................ 514/11, 16, 17, 514/863; 530/317, 328, 329, 333

(56) References Cited

U.S. PATENT DOCUMENTS

| 5,229,366 | 7/1993 | Tsukada et al. . |
| 5,510,332 | 4/1996 | Kogan et al. . |

FOREIGN PATENT DOCUMENTS

| 0341915 | 11/1989 | (EP) . |
| 0422938 | 4/1991 | (EP) . |
| WO 92/00995 | 1/1992 | (WO) . |
| WO 94/02445 | 2/1994 | (WO) . |
| WO 94/15958 | 7/1994 | (WO) . |
| WO 95/14714 | 6/1995 | (WO) . |
| WO 95/15973 | 6/1995 | (WO) . |
| 96/00581 | 1/1996 | (WO) . |
| WO 96/06108 | 2/1996 | (WO) . |
| 96/20216 | 7/1996 | (WO) . |
| 9620216 * | 7/1996 | (WO) .............................. C07K/14/78 |

OTHER PUBLICATIONS

Wayner: "Activation–dependent recognition by hematopoietic cells of the LDV sequence in the V region of fibronectin", Journal of Cell Biology, vol. 116, No. 2, 1992, pp. 489–497, cited in the application, see the whole document.
Kiso: "Synthesis of ANP fragments with hypertensive action", Chemical Abstracts, vol. 110, No. 3, Jan. 16, 1989; abstract No. 24283k, p. 592, col. 1; see abstract & Pept.Chem.,–1987 pp. 512–516.
B.Weinstein; "Chemistry and Biochemistry of Amino Acids, Peptides and Proteins", 1983, See p. 338–p. 341.
Aumailley et al., "Arg–Gly=Asp constrained within cyclic pentapeptides—Strong and selective inhibitors of cell adhesion of vitronectin and laminin fragment P1", Federation of European Biochemical Societies, Oct., 1991, pp. 50–54.

Lublin, "Susceptibility to experimental allergic encephalomyelitis in animal models of autoimmunity", Neurology and Neurosurgery, 1992, vol. 5, pp. 182–187.
Bowen et al., "Disease–Modifying Anti–Rheumatic Drugs: Strategies for Screening", Pharmac. Ther. 1992, vol. 56, pp. 287–306.
Nakajima et al., Role of Vascular Cell Adhesion Molecule 1/Very Late Activation Antigen 4 and Intercellular Adhesion Molecule 1/Lymphocyte Function–associated Antigen 1 Interactions in Antigen–induced Eosinophil and T Cell Recruitment into the Tissue. J. Exp. Med. Apr., 1994, pp. 1145–1154.
Pretolani et al., Antibody to Very Late Activation Antigen 4 Prevents Antigen–induced Bronchial Hyperreactivity and Cellular Infiltration in the Guinea Pig Airways, J. Exp. Med., Sep. 1994, pp. 795–805.
Vanderslice et al., A Cyclic Hexapeptide Is a Potent Antagonist of $\alpha_4$ Integrins, J. Immunology, 185 (1997), pp. 1710–1718.
Yang, et al., "Interaction of Monocytoid Cels with the Mucosal Addressin MAdCAM–1 via Integrins VAL–4 and LPAM–1." Abstract, Immunol Cell Biol. 1996, 74(5), 383–393; abstract No. 1996:696526.*

* cited by examiner

Primary Examiner—Karen Cochrane Carlson
Assistant Examiner—Anish Gupta
(74) Attorney, Agent, or Firm—Pillsbury Winthrop LLP

(57) ABSTRACT

Cyclic peptide of formula (1) where $Xaa_1$ is selected from L-amino acids selected from Phe, Lys and Arg, D-amino acids selected from Phe and Met, the L- and D-amino acid optionally substituted on its α-carbon or its α-amino group with a $C_{1-4}$ alkyl group; and MeIle; $Xaa_2$, $Xaa_3$ et $Xaa_4$ are respectively Leu, Asp and Val, optionally substituted on their α-carbon or α-amino group with a $C_{1-4}$ alkyl group; $X^1$ is selected from D-amino acids selected from Ala, Phe, Arg, Lys, Trp, $hArg(Et)_2$, $Orn(CHMe_2)$, $Orn(Me_2)$, $Lys(CHMe_2)$ and Arg(Pmc), optionally substituted on their α-carbon or α-amino group with a $C_{1-4}$ alkyl group; Formula (II); $NH(CH_2)_5CO$; and $NH(CH_2)_2S(CH_2)_yCO$, where y is 1 or 2; $X^2$ is selected from D-amino acids selected from Ala, Arg, Lys, His, $hArg(Et)_2$, $Orm(CHMe_2)$, and $Om(Me_2)$, optionally substituted on their α-carbon or α-amino group with a $C_{1-4}$ alkyl group; $NH(CH_2)_2SCH_2CO$; and $NH(CH_2)_xCO$, where x is 2 or 3; $Xaa_5$ and $Xaa_6$ are each independently a D-amino acid selected from Ala and Arg, optionally substituted on its α-carbon or α-mino group with a $C_{1-4}$ alkyl group; p is 0 or 1; and q is 0 or when p is 1, q is 0 or 1; or a salt thereof. The cyclic peptides inhibit the interaction of vascular cell adhesion molecule–1 and fibronectin with integrin very late antigen 4 ($\alpha 4\beta 61$) and of mucosal addressin cell adhesion molecule–1 (MAdCAM–1) with integrin $\alpha 4\beta 7$. They have therapeutic applications such as in rheumatoid arthrids, multiple sclerosis, astlna, psoriasis, inflammatory bowel disease and insulin-dependent diabetes.

19 Claims, 5 Drawing Sheets

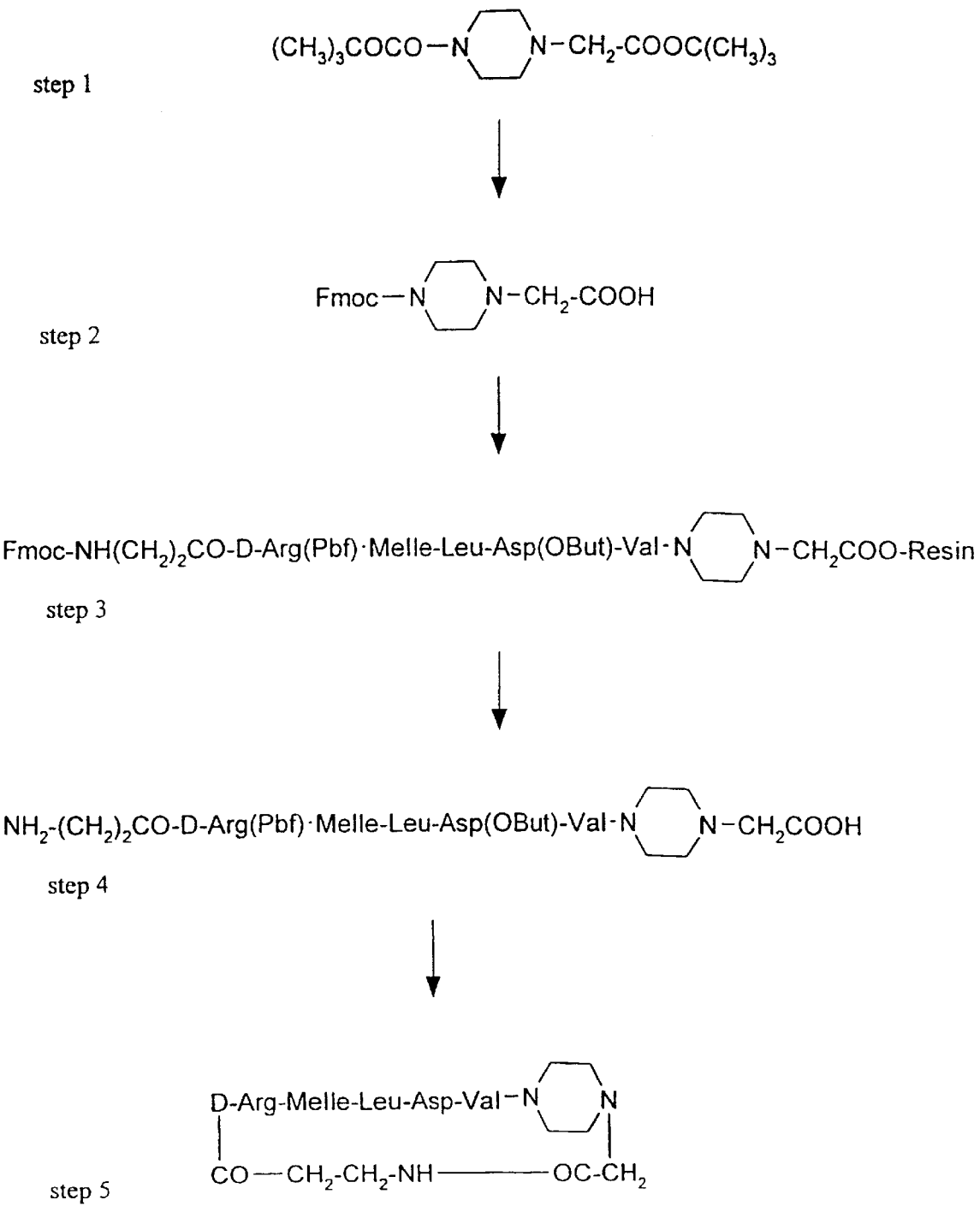

Fig.2.

Step 1

Fmoc—Val-Chlorotritylresin

Step 2.

Fmoc-D-Arg(Pmc)-MeIle-Leu—Asp(OBut)-Val-D-Ala-D-Ala-Chlorotritylresin

| Piperidine

Step 3

D-Arg(Pbf)-D-Arg(Pbf)—MePhe-Leu-Asp(OBut)-Val-Chlorotritylresin

| Acetic acid/Trifluoroethanol/
| Dichloromethane

Step 4.

D-Arg(Pbf)-D-Arg(Pbf)—MePhe-Leu-Asp(OBut)-Val

| Cyclisation

Step 5.

c(D-Arg(Pbf)-D-Arg(Pbf)—MePhe-Leu-Asp(OBut)-Val)

| Trifluoroacetic acid/water/
| Triisopropylsilane

Step 6.

c(MePhe-Leu-Asp-Val—D-Arg-D-Arg)

Fig.3.

Step 1

Fmoc—D-Ala-Chlorotritylresin

Step 2.

Fmoc-D-Arg(Pmc)-MeIle-Leu—Asp(OBut)-Val-D-Ala-D-Ala-Chlorotritylresin

Piperidine

Step 3

D-Arg(Pmc)-MeIle-Leu-Asp(OBut)—Val-D-Ala-D-Ala-Chlorotritylresin

Acetic acid/Trifluoroethanol/
Dichloromethane

Step 4.

D-Arg(Pmc)-MeIle-Leu-Asp(OBut)—Val-D-Ala-D-Ala

Cyclisation

Step 5.

c(D-Arg(Pmc)-MeIle-Leu—Asp(OBut)-Val-D-Ala-D-Ala)

Trifluoroacetic acid/water/
Triisopropylsilane

Step 6.

c(D-Ala-D-Ala-D-Arg-MeIle—Leu-Asp-Val)

CELL ADHESION IHIBITING COMPOUNDS

Many of the cell-cell and cell-extracellular matrix interactions are mediated by protein ligands (e.g. fibronectin, vitronfectin and VCAM-1) and their integrin receptors [e.g. VLA-4 (α4β1)]. Recent studies have shown these interactions to play an important role in many physiological (e.g. embryonic development and wound healing) and pathological (e.g. tumour-cell invasion and metastasis, inflammation, atherosclerosis and autoimmune diseases) conditions. Agents which can selectively inhibit some of these interactions are predictably useful for the treatment of a number of diseases.

Integrins are heterodimeric cell surface receptors that are composed of noncovalently associated α and β subunits. Using molecular biology and protein chemistry, a number of α and β subunits have been identified. The integrin family can be subdivided into classes based on the β subunits, which can be associated with one or more α subunits. The most widely distributed integrins belong to the β1 class, also known as the very late antigens (VLA). The second class of integrins are leukocyte-specific receptors and consist of one of three a subunits (αL, αM, or αX) complexed with the β2 protein. The cytoadhesins αIIbβ3 and αvβ3, constitute a third class of integrins. A fourth class of integrins includes α4β7.

A wide variety of proteins serve as ligands for integrin receptors. In general, the proteins recognised by integrins fall into one of three classes: extracellular matrix proteins, plasma proteins, and cell surface molecules. Extracellular matrix proteins such as collagen, fibronectin, fibrinogen, laminin, thrombospondin, and vitronectin bind to a number of integrins. Many of these adhesive proteins also circulate in plasma and bind to activated blood cells. Additional components in plasma that are ligands for integrins include fibrinogen and factor X. Cell-bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins. Mucosal addressin cell adhesion molecule-1 (MAdCAM-1) is another member of the Ig superfamily and is bound by the integrin α4β7.

The target amino acid sequences for many integrins have been identified. For example, the target sequence in α5β1, αIIβ3, and αvβ3, is the Arg-Gly-Asp tripeptide found in proteins such as fibronectin, fibrinogen, thrombospondin, type 1 collagen, vitronectin and vWF. However, the Arg-Gly-Asp sequence is not the only integrin recognition motif used by adhesive ligands. Another integrin α4β1 binds the variable region (CS1) of fibronectin via the sequence Leu-Asp-Val and the platelet integrin αIIbβ3 also recognises the sequence His-His-Leu-Gly-Gly-Ala-Lys-Gln-Ala-Gly-Asp-Val at the carboxy-terminus of the gamma chain of fibrinogen.

The present invention principally relates to agents which block the interaction of the ligand VCAM-1 to its integrin receptor VLA-4 (α4β1). [Reference for a review on VLA-4: Structure of the Integrin VLA-4 and Its Cell—Cell and Cell Matrix Adhesion Functions, M. E. Hemler, M. J. Elices, C. Parker and Y. Takada, Immunological Reviews, 114 (1990) 45–65.] Integrin α4β1 is expressed on numerous hematopoietic cells and established cell lines, including hematopoietic precursors, peripheral and cytotoxic T lymphocytes, B lymphocytes, monocytes, thymocytes and eosinophils. Unlike other β1 integrins that are involved only in cell—extracellular matrix interactions, α4β1 mediates both cell—cell and cell-extracellular matrix interactions. Cells expressing activated α4β1 bind to the carboxy-terminal cell binding domain of fibronectin (non Arg-Gly-Asp mediated), to VCAM-1 expressed on endothelial cells, and to each other to promote homotypic aggregation. The expression of VCAM-1 by endothelial cells is upregulated by proinflammatory cytokines such as INF-γ, TNF-αand IL-1β.

The present invention also relates to agents which block the interaction of the ligand MAdCAM-1 and the integrin α4β7.

Regulation of α4β1-mediated cell adhesion is important in numerous physiologic processes, including T-cell proliferation, B-cell localisation to germinal centres, and adhesion of activated T cells and eosinophils to endothelial cells. In addition, integrin α4β1-mediated processes have been implicated in tumour cell metastasis and diseases involving lymphocyte, monocyte or eosinophil recruitment such as multiple sclerosis, rheumatoid arthritis, asthma, psoriasis, insulin-dependent diabetes, glomerulonephritis, inflammatory bowel disease, ischaemic heart disease, myocarditis, peripheral vascular disease, transplant rejection, for example chronic allograft rejection, and allergic disorders. Evidence for the involvement of VLA-4VCAM-1 interaction in the above disease processes has been accumulated by investigating the role of the peptide CS-1 and antibodies specific for VLA-4 or VCAM-1 in various in vitro and in vivo experimental models of inflammation (e.g. contact cutaneous hypersensitivity response in mice), experimental autoimmune encephalomyelitis, lung antigen challenge, diabetes, ulcerative colitis, nephritis and allograft rejection. Additionally, integrin α4β7-mediated processes have been implicated in lymphocyte recruitment in diseases such as inflammatory bowel disease and insulin-dependent diabetes.

For example, in an experimental model of arthritis (arthritis induced in inbred female Lewis rats with a single intraperitoneal injection of peptidoglycan-polysaccharide fragments from group A streptococcal cell walls), intravenous administration of CS-1 at the initiation of arthritis (days 0–4; 300 μg/day) or on days 11 to 16 in animals with established arthritis, was shown to suppress both acute and chronic inflammation. [Reference: Synthetic Fibronectin Peptides Suppress Arthritis in Rats by Interrupting Leukocyte Adhesion and Recruitment, S. M. Wahl, J. B. Allen, K. L. Hines, T. Imamichi, A. M. Wahl, L. T. Furcht and J. B. McCarthy, J. Clin. Invest, 94 (1994) 655–662].

In another model of inflammation (contact hypersensitivity response in oxazalone or 2.4-dinitrofluorobenzene-sensitised mice), intravenous administration of the anti-α-4 specific monoclonal antibodies R1-2 or PS/2 (4 to 6 hours prior to challenge) significantly inhibited (50–60% reduction in the ear swelling response) the efferent response. [Reference:

Monoclonal Antibodies to the Integrin α-4 Subunit Inhibit the Murine Contact Hypersensitivity Response, P. L. Chisholm, C. A. Williams and R. R. Lobb, Eur. J. Immunol., 23 (1993) 682–688]. In an intestinal inflammation model (acute colitis in Cotton-top tamarin), anti-α4 integrin monoclonal antibody HP1/2 that binds VLA4 resulted in significant attenuation of acute colitis. In contrast, two anti-E-selectin monoclonal antibodies (BB11 and EH8) slightly diminished colitis after the 10-day treatment period in Cotton-top tamarin [Reference: Attenuation of Colitis in the Cotton-top Tamarin by Anti-α 4 Integrin Monoclonal Antibody, D. K. Podolsky, R. Lobb, N. King, C. D. Benjamin, B. Pepinsky, P. Sehgal and M. deBeaumont, J. Clin. Invest., 92 (1993) 372–380].

The antibodies have also been shown to be effective in a model of autoimmune encephalomyelitis (EAE). EAE is an inflammatory condition of the central nervous system with similarities to multiple sclerosis. In the model the inflammation is induced experimentally. In both EAE and multiple sclerosis, circulating leukocytes penetrate the blood-brain barrier and damage myelin, resulting in impaired nerve conduction and paralysis. EAE can be induced actively by priming an animal to CNS proteins like myelin basic protein (MBP), or adoptively by injection of activated lymphocytes that are specific for these CNS antigens. Various monoclonal antibodies, MK/1 (anti-VCAM-1) and PS/2 and LPAM-1 (anti α4 integrin), when injected into irradiated female (PL/IJxSJL)F1 mice delayed the onset of disease. When injection of antibody to $a^4$ integrin (i.e. LPAM-1 and PS/2) was continued every 3 days until after onset of disease, not only was the onset of disease delayed, but in this case severity of disease was also significantly decreased. [Reference: Surface Expression of α 4 Integrin by CD4 T Cells Is Required for Their Entry into Brain Parenchyma, J. L. Baron, J. A. Madri, N. H. Ruddle, J. Hashim and C. A. Janeway, Jr., J. Exp. Med., 177 (1993) 57–68].

Monoclonal antibodies to VCAM-1 (M/K-1) and VLAA (PS-2) have also been shown to be active in experimental asthma models (antigen-induced eosinophil and T-cell recruitment). Both these antibodies when injected intraperitoneally 24 hours before the inhaled ovalbumin challenge significantly decreased (73–74%) eosinophil infiltration in mice [Reference: Role of vascular cell adhesion molecule–1/very late activation antigen 4 and intracellular adhesion molecule 1/lymphocyte function-associated antigen 1 interactions in antigen-induced eosinophil and T-recruitment into the tissue, H. Nakajima, H. Sano, T. Nishimura, S. Yoshida and I. Iwamoto, J Exp. Med., 179 (1994) 1145–1154]. Similar results were obtained in guinea pigs when anti-VLA-4 monoclonal antibody HP1/2 was injected (3–10 mg/kg) before ovalbumin challenge [Reference: Antibody to very late activation antigen 4 prevent antigen -induced bronchial hyperreactivity and cellular infiltration in the guinea-pig airways, M. Pretolani, C. Ruffie, J-R Lapa e Silva, D. Joseph, R. R. Lobb and B. B. Vargaftig, J. Exp. Med., 180 (1994), 795–805 and Role of the VLA-4 integrin in leukocyte recruitment and bronchial hyperresponsiveness in the guinea-pig, A. A. Y. Milne and P. J. Piper, European J Pharmacol., 282 (1995), 243–249].

Antibodies specific for both α4-integrin (LPAM-1) and one of its ligands, VCAM-1, were also shown to be effective in treating insulin-dependent diabetes mellitus in the nonobese diabetic mouse. Insulin-dependent diabetes mellitus is believed to be an autoimmune disease in which activated T lymphocytes destroy the insulin-producing β-cells of the pancreatic islets. The antibody R1-2 prevented the onset of insulitis in a dose-dependent manner in nonobese diabetic mice. The blocking of disease was accompanied by a marked decrease in lymphocytic infiltration of the islets of Langerhans. [Reference: The Pathogenesis of Adoptive Murine Autoimmune Diabetes Requires an Interaction Between α 4-Integrins and Vascular Cell Adhesion Molecule–1, J. L. Baron, E-P. Reich, I. Visintin and C. A. Janeway, Jr., J. Clin. Invest., 93 (1994) 1700–1708].

Cells expressing integrin α4β1 have been shown to bind to sequences in the heparin II binding domain and the alternatively spliced type III connecting segment (IIICS) located in the carboxy-terminal cell binding domain of fibronectin. Within the IIICS region, α4β1 binds with high affinity to a peptirde sequence termed CS-1 (a 25-amino acid peptide), suggesting that this is the major site of α4β1 interaction in fibronectin. The tripeptide Leu-Asp-Val is the minimal sequence within CS-1 capable of supporting hematopoietic cell adhesion or of inhibiting α4β1-mediated cell binding to fibronectin. [References for CS1: The Minimal Essential Sequence for a Major Cell Type-Specific Adhesion Site (CS1) Within the Alternatively Spliced Type III Connecting Segment Domain of Fibronectin is Leucine-Aspartic Acid-Valine, A. Komoriya, L. J. Green, M. Mervic, S. S. Yamada, K. M. Yamada and M. J. Humphries, J. Biol. Chem., 23 (1991) 15075–15079; Activation-Dependent Recognition by Hematopoietic Cells of the LDV Sequence in the V Region of Fibronectin, E. A. Wayner and N. L. Kovach, J. Cell Biol., 116 (1992) 489–497.]

In addition to the Leu-Asp-Val containing sequences mentioned above, a cyclic octapeptide 1-adamantaneacetyl-Cys-Gly-Arg-Gly-Asp-Ser-Pro-Cys (containing a disulphide bridge between the two cysteine residues) has been reported to be as effective as the LDV containing peptide Cys-Leu-His-Gly-Pro-Glu-Ile-Leu-Asp-Val-Pro-Ser-Thr in blocking Jurkat cell adhesion to CS-1 coated plates (IC$_{50}$ 30 μM). The cyclic peptide also inhibited the binding of Jurkat cells to fibronectin coated plates. In addition to inhibiting α4β1-induced adhesion, the octapeptide also inhibited function in αvβ3 as well as αIIbβIIIa-dependent assays. Therefore the peptide is not selective for α4β1-mediated adhesion. [Reference: Cyclic RGD Peptide Inhibits α4β1 Interaction with Connecting Fragment 1 and Vascular Cell Adhesion Molecule, P. M. Cardarelli, R. R. Cobb, D. M. Nowlin, W. Scholz, F. Gorcsan, M. Moscinski, M. Yasuhara, S-L. Chiang and T. J. Lobl, J. Biol. Chem., 269 (1994) 18668–18673.]

A few small non-peptidic compounds [Reference: Non-peptidic Surrogates of the Leu-Asp-Val Sequence and Their Use in the Treatrnent of Inflammation, Autoimmune Diseases and Tumour progression, YEDA Research and Development Co. Ltd, WO 94/02445, Publ. date Feb. 3, 1994] have also been reported to inhibit α4β1-induced adhesion.

Furthermore, in WO 96/00581, Publi. date Jan. 11, 1996, a number of cyclic peptides containing the Leu-Asp-Val sequence and at least one Cys amino acid residue and/or a Glu amino acid residue have been reported to inhibit the binding of α4β1 integrin to VCAM-1 or fibronectin. However, three of the cyclic peptides disclosed in this patent application (namely, c(Glu-TripLeu-Asp-Val), c(Glu-Trp-Leu-Asp-Val-Asp) and c(Glu-Trp-Leu-Asp-Val-Pro-Glu-Trp-Leu-Asp-Val), where c indicates the amino acid sequence is cyclised), were shown to te very poor inhibitors of the binding of HL-60 cells to VCAM-1-IgG fusion protein (IC$_{50}$ values of 94,>1000 and>1000 μM respectively). [Reference: P. Vanderslice, K. Ren, J. K. Revelle, D. C. Kim, D. Scott, R. J. Bjercke, E. T. H. Yeh, P. J. Beck and T. P. Kogan, J. Immunology, 158, (1997), 1710–1718].

A disulphide cyclic pentapeptide, Arg-Cys-Asp-thioproline-Cys (thioproline=thiazolidine-4-carboxylic acid), has also been reported to be an inhibitor of leukocyte cell adhesion to fibronectin. In addition, the cyclic peptide also inhibited the binding to the 120 kDa chymotryptic fragment of fibronectin, which contains the Arg-Gly-Asp central cell binding domain. Again, the peptide was not selective binding to both α4β1 and α5β1 [Reference: A Novel Cyclic Pentapeptide Inhibits α4β1 and α5β1 Integrin-Mediated Cell Adhesion, D. M. Nowlin, F. Gorcsan, M. Moscinski, S-L. Chiang, T. J. Lobl and P. M. Cardarelli, J. Biol. Chem., 268 (1993) 20352–20359.]

In our copending PCT application, WO96/20216, Publi. date Jul. 4, 1996, cyclic peptides containing the Leu-Asp- Val sequence which inhibit the binding of α4β1 integrin to VCAM-1 or fibronectin are reported.

Although a number of peptides that inhibit the interaction of VCAM-1 and fibronectin with integrin VLA4 have been discovered, there is a continuing need for alternative compounds which inhibit this interaction and, in particular, for compounds which can be formulated into slow release pharmaceutical compositions. There is also a need for compounds which inhibit the interaction of MAdCAM-1 with the integrin α4β7.

According to one aspect of the present invention there is provided a cyclic peptide of formula

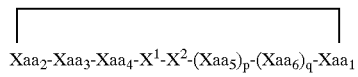

Xaa$_2$-Xaa$_3$-Xaa$_4$-X$^1$-X$^2$-(Xaa$_5$)$_p$-(Xaa$_6$)$_q$-Xaa$_1$ where

Xaa$_1$ is selected from L-amino acids selected from Phe, Lys and Arg; D-amino acids selected from Phe and Met, the L- and D-amino acid optionally substituted on its α-carbon or its α-amino group with a C$_{1-4}$ alkyl group; and MeIle; Xaa$_2$ is Leu, optionally substituted on its α-carbon or α-amino group with a C$_{1-4}$ alkyl group; Xaa$_3$ is Asp, optionally substituted on its α-carbon or α-amino group with a C$_{1-4}$ alkyl group; Xaa$_4$ is Val, optionally substituted on its α-carbon or α-amino group with a C$_{1-4}$ alkyl group; X$^1$ is selected from D-amino acids selected from Ala, Phe, Arg, Lys, Trp, hArg(Et)$_2$, Orn(CHMe$_2$), Orn(Me$_2$), Lys(CHMe$_2$) and Arg(Pmc), optionally substituted on their α-carbon or their α-amino group with a C$_{1-4}$ alkyl group;

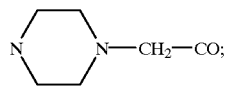

NH(CH$_2$)$_5$CO; and NH(CH$_2$)$_2$S(CH$_2$)$_y$CO, where y is 1 or 2;

X$^2$ is selected from D-amino acids selected from Ala, Arg, Lys, His, hArg(Et)$_2$, Orn(CHMe$_2$), and Orn(Me$_2$), optionally substituted on their α-carbon or their α-amino group with a C$_{14}$ alkyl group; NH(CH$_2$)$_2$SCH$_2$CO; and NH(CH$_2$)$_x$CO, where x is 2 or 3;

Xaa$_5$ and Xaa$_6$ are each, independently a D-amino acid selected from Ala and Arg, optionally substituted on its α-carbon or α-amino group with a C$_{1-4}$ alkyl group;

P is 0 or 1; and q is 0 or when p is 1,q is 0 or 1;

or a salt thereof;

with the proviso that when Xaa$_1$ is MeIle, Xaa$_2$ is Leu, Xaa$_3$ is Asp, Xaa$_4$ is Val and p and q are both 0, i) X$^2$ is not D-Ala, D-Arg, or D-Lys when X$^1$ is D-Ala;
ii) x$^2$ is not D-Arg when X$^1$ is

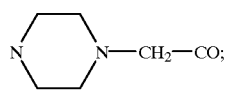

iii) X$^2$ is not D-Ala, D-Arg or D-His when X$^1$ is D-Arg;
iv) X$^2$ is not D-Ala when X$^1$ is D-Orn (CHMe$_2$) or D-Arg(Pmc);
v) X$^2$ is not D-Ala or D-Lys when X$^1$ is D-Lys; and
vi) X$^2$ is not D-Lys or D-Arg when X$^1$ is D-Phe or D-Trp.

The cyclic peptides preferably have an IC$_{50}$ of <10 μM, more preferably <5 μM in the MOLT-4 cell-fibronectin assay hereinafter described or an IC$_{50}$<30 μM, more preferably <5 μM in the MOLT-4 cell/recombinant soluble VCAM-1 assay hereinafter described.

The cyclic peptides are also active in the JY cell/MAdCAM-1 Adhesion assay, hereinafter described.

It is to be understood that amino acids have the L-configuration unless otherwise stated and that all residue components, that is Xaa$_1$ to Xaa$_6$ X$^1$ and X$^2$ forming the cyclic peptides are written left to right in the direction from the amino (N-terminus) to the carboxyl (C-terminus) groups. The residue components are linked together so that the carboxyl terminus of one residue is linked to the amino terminus of the adjacent residue. Where a naturally occurring amino acid has more than one carboxyl and/or amino group, linking is respectively through the ac-carboxyl and the α-amino groups. Linking for the residues D-hArg(Et)$_2$, D-Orn(CHMe$_2$), D-Orn(Me$_2$), D-Lys(CHMe$_2$) and D-Arg (Pmc) is hereinafter defined with respect to the figures. The naturally occurring amino acids residues in the cyclic peptides are generally defined in terms of a three letter code where Ala is alanine, His is histidine, Ile is isoleucine, Lys is lysine, Arg is arginine, Val is valine, Asp is aspartic acid, Met is methionine, Phe is phenylalanine, Leu is leucine, and Trp is tryptophan. MePhe and MeIle respectively refer to N-methyl phenylalanine and N-methyl isoleucine. D-hArg (Et)$_2$, D-Orn(CHMe$_2$), D-Orn(Me$_2$), D-Lys(CHMe$_2$) and D-Arg(Pmc) are hereinafter defined in the figures.

It is to be understood that generic terms such as 'alkyl' include both straight and branched chain variants. Compounds of the present invention include solvates such as for example hydrates and include prodrugs such as, for example, in vivo hydrolysable esters.

Preferably Xaa$_1$ includes L-MeIle, L-MePhe, L-Lys, L-Arg, D-Phe and D-Met. Preferred values for Xaa$_2$, Xaa$_3$ and Xaa$_4$ are respectively Leu, Asp, and Val. X$^1$ is preferably selected from D-amino acids selected from Ala, Phe, Arg, Lys, Trp, hArg(Et)$_2$, Orn(CHMe$_2$), Orn(Me$_2$), Lys(CHMe$_2$) and Arg(Pmc); and

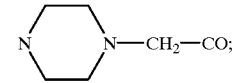

NH(CH$_2$)$_5$CO; and NH(CH$_2$)$_2$S(CH$_2$)$_y$CO, where y is 1 or 2.
x$^2$ is preferably selected from D-amino acids selected from Ala, Arg, Lys, His, hArg(Et)$_2$, Orn(CHMe$_2$), and Orn(Me$_2$); NH(CH$_2$)$_2$SCH$_2$CO, and NH(CH$_2$)$_x$CO, where x is 2 or 3. Xaa$_5$ and Xaa$_6$ are preferably each, independently D-Ala or D-Arg.

Cyclic peptides or salts thereof in which any two of X$^1$, X$^2$, (Xaa$_5$)$_p$ and (Xaa$_6$)$_q$ are D-Arg represent a particularly preferred aspect of the invention.

According to a further aspect of the invention, cyclic peptides have the formula formula

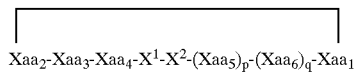

Xaa$_2$-Xaa$_3$-Xaa$_4$-X$^1$-X$^2$-(Xaa$_5$)$_p$-(Xaa$_6$)$_q$-Xaa$_1$ where

Xaa$_1$ is selected from L-amino acids selected from Phe, Lys and Arg; D-amino acids selected from Phe and Met, the L- and D-amino acid optionally substituted on its α-carbon or its α-amino group with a C$_{1-4}$ alkyl group; and MeIle; and most preferably is MePhe;

Xaa$_2$ is Leu, optionally substituted on its α-carbon or α-amino group with a C$_{1-4}$ alkyl group;

Xaa$_3$ is Asp, optionally substituted on its α-carbon or α-amino group with a C$_{1-4}$ alkyl group;

Xaa$_4$ is Val, optionally substituted on its α-carbon or α-amino group with a C$_{1-4}$ alkyl group;

X$^1$ is selected from D-amino acids selected from Ala, Phe, Arg, Lys and Trp, optionally substituted on their α-carbon or their α-amino group with a C$_{1-4}$ alkyl group, hArg(Et)$_2$, Orn(CHMe$_2$), OM(Me$_2$), Lys (CHMe$_2$) and Arg(Pmc); and

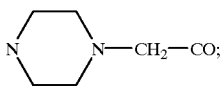

NH(CH$_2$)$_5$CO; and NH(CH$_2$)$_2$S(CH$_2$)$_y$CO, where y is 1 or 2;

X$^2$ is selected from D-amino acids selected from Ala, Arg, Lys and His, optionally substituted on their α-carbon or their α-amino group with a C$_{1-4}$ alkyl group, hArg(Et)$_2$, Orn(CHMe$_2$), and Orn(Me$_2$); NH(CH$_2$)$_2$SCH$_2$CO; and NH(CH$_2$)$_x$CO, where x is 2 or 3;

Xaa$_5$ and Xaa$_6$ are each, independently a D-amino acid selected from Ala and Arg, optionally substituted on its α-carbon or α-amino group with a C$_{1-4}$ alkyl group;

p is 0 or 1; and q is 0 or when p is 1, q is 0 or 1; or a salt thereof; with the proviso that when p and q are both 0, Xaa$_1$ is not MeIle; or a salt thereof In such a cyclic peptide when Xaa$_1$ is MeIle, p is 1 and q is either 0 or 1.

According to yet a further aspect of the invention cyclic peptides have the formula

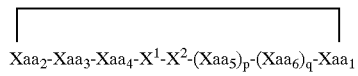

where

Xaa$_1$ is a L-amino acid selected from MePhe and MeIle;

Xaa$_2$ is Leu, optionally substituted on its α-carbon or α-amino group with a C$_{1-4}$ alkyl group;

Xaa$_3$ is Asp, optionally substituted on its α-carbon or α-amino group with a C$_{1-4}$ alkyl group;

Xaa$_4$ is Val, optionally substituted on its α-carbon or α-amino group with a C$_{1-4}$ alkyl group;

X$^1$ is selected from D-amino acids selected from Ala and Arg, optionally substituted on their α-carbon or their α-amino group with a C$_{1-4}$ alkyl group;

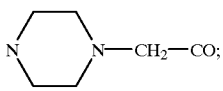

and NH(CH$_2$)$_2$S(CH$_2$)$_y$CO, where y is 1 or 2;

X$^2$ is selected from D-amino acids selected from Ala and Arg optionally substituted on their α-carbon or their α-amino group with a C$_{1-4}$ alkyl group; and NH(CH$_2$)$_x$CO, where x is 2 or 3;

Xaa$_5$ and Xaa$_6$ are each, independently a D-amino acid selected from Ala and Arg, optionally substituted on its α-carbon or α-amino group with a C$_{1-4}$ alkyl group;

p is 1;and q is 0 or 1;

or a salt thereof.

Particularly preferred cyclic peptides according to the invention are cyclic peptides having any of the structures of compounds 1–38 in Table 2 hereinafter; or a salt thereof. Any amino acid in structures 1–38 is optionally substituted on its α-carbon or α-amino group with C$_{1-4}$ alkyl (especially methyl). Preferred cyclic peptides are any of compounds 8, 20–23, 25–32, 37 and 38. More preferred cyclic peptides are any of compounds 20, 21, 27 and 31.

The cyclic peptides of the present invention have at least one of the following advantages: they are more potent than known compounds, e.g. CS-1 (a 25-amino acid peptide) in our tests; they are smaller than CS-1, and therefore easier to synthesise, and being cyclic are more stable to enzymic degradation; and they are compatible with slow release pharmaceutical compositions.

Preferred compounds have shown activity in a number of in vivo screens in mice, for example, delayed-type hypersensitivity responses induced by oxazolone in the skin (contact hypersensitivity, CHS, or by ovalbumin in the footpad (delayed-type hypersensitivity, DTH), collagen-induced arthritis, antigen-induced bronchiolar lavage eosinophilia and experimental allergic encepholmyelitis. For example, the dose of CS-1 required to produce a half-maximal inhibitory response in DTH was 1 mg/kg/day while that for compound 20 was 0.01 mg/kg/day. No toxicity at the effective dose was observed for the compounds of the present invention.

According to a further feature of the invention there is provided a pharmaceutical composition which comprises a cyclic peptide of the invention in association with a pharmaceutically acceptable diluent or carrier. The invention also provides a pharmaceutical composition which comprises a pharmaceutically acceptable salt of a cyclic peptide according to the invention in association with a pharmaceutically acceptable diluent or carrier.

Pharmaceutically acceptable salts include, for example, for cyclic peptides that are sufficiently basic, for example, those having a free guanidino group such as arginine, salts with acids forming physiologically acceptable anions, such as salts with mineral acids, for example, hydrogen halides such as hydrogen chloride and hydrogen bromide, sulphonic and phosphonic acids; and with organic acids, especially acetic, oxalic, tartaric, mandelic, p-toluenesulphonic, methanesulphonic acids and the like. For cyclic peptides which are sufficiently acidic, for example those having a free carboxylic acid group, salts with bases forming physiologically acceptable cations such as salts with alkali metal such as sodium and potassium; alkaline earth metals such as magnesium and calcium; aluminium and ammonium salts, and salts with organic bases such as ethanolamine, methylamine, diethylamine, isopropylamine, trimethylamine and the like. Such salts may be prepared by any suitable method known in the art.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension, or a depot formulation with drug incorporated in a biodegradable polymer. The composition may be in a form suitable for topical administration such as for example creams, ointments and gels. Skin patches are also contemplated. Formulation in general is described in Chapter 25.2 of Comprehensive Medicinal Chemistry, Volume 5, Editor Hansch et al, Pergamon Press 1990.

In general the above compositions may be prepared in a conventional manner using conventional excipients. However, in the case of a composition for oral administration, it may be convenient for the composition to include a coating to protect the cyclic peptide active ingredient from the actions of enzymes in the stomach.

A preferred composition of the invention is one suitable for oral administration in unit dosage form for example a tablet or capsule. Which contains from 2.5 to 500 mg, and preferably 10 to 100 mg, of cyclic peptide in each unit dose, or one suitable for parenteral administration which contains from 0.5 to 100 mg of cyclic peptide per ml, and preferably 1 to 10 mg of cyclic peptide per ml of solution.

A parenteral composition is preferably a solution in isotonic saline or isotonic dextrose buffered if necessary to a pH of 5 to 9. Alternatively, the parenteral composition may be one designed for slow release in which case the amount of cyclic peptide per unit dose is in general greater than that required when a conventional injectable formulation is used. A preferred slow release formulation is a continuous release formulation, for example a formulation of the type described in European Patent Specification No. 58481. For slow release formulations containing polylactic/polyglycolic based polymers it is preferred that the cyclic peptide of the invention contains a basic group. For such cyclic peptides an alternative slow release formulation is as described in International Patent Application, Publication No. WO93/24150. A basic amino acid is defined as one containing a basic functional group in its side chain, such as for example amino or guanidino either of which may be optionally substituted with $C_{1-4}$ alkyl. One such particularly preferred basic amino acid is arginine. In a particularly preferred embodiment of the invention in the cyclic peptide of formula I any two of $X^1$, $X^2$, $(Xaa_5)_q$ and $(Xaa_6)_q$ are D-Arg. Such cyclic peptides containing a basic amino acid can form so-called 'peptide-polymer' salts with acid ended polyesters, for example polylactides. These salts have advantageous solubility characteristics which makes them particularly suitable for manufacturing slow release parenteral formulations which have beneficial release profiles and are stable on storage. A preferred slow release parenteral formulation contains from 1 to 100 mg of cyclic peptide per unit dose. A preferred pharmaceutical composition is for parenteral administration designed for slow release over a period of at least 5 days.

The composition of the invention will normally be administered such that a daily oral dose will be from 0.1 mg/kg, to 50 mg/kg and a daily parenteral dose, will be from 5, preferably from 20, micrograms/kg to 10 mg/kg.

According to a further feature of the invention there is provided a method for inhibiting the interaction between VCAM-1 and/or fibronectin and the integrin receptor VLA-4 in warm-blooded mammals, such as man, in need of such treatment which comprises administering to said animal an effective amount of a cyclic peptide of the invention or a pharmaceutically acceptable salt thereof. The invention also provides the use of such a cyclic peptide or a pharmaceutically-acceptable salt thereof in the production of a new medicament for use in the treatment of a disease ominedical condition mediated by the interaction between fibronectin and/or VCAM-1 (especially VCAM-1) and the integrin receptor VLA4. Utility as tools for research is also contemplated.

According to a further aspect of the invention there is provided a method for inhibiting the interaction between MAdCAM-1 and the integrin $\alpha 4 \beta 7$ in warm-blooded mammals, such as man, in need of such treatment which comprises administering to said animal an effective amount of a cyclic peptide of the invention or a pharmaceutically acceptable salt thereof. The invention also provides the use of such a cyclic peptide or a pharmaceutically-acceptable salt thereof in the production of a new medicament for use in the treatment of a disease or medical condition mediated by the interaction between MAdCAM-1 and the integrin $\alpha 4 \beta 7$. Utility as tools for research is also contemplated.

According to another aspect of the present invention there is provided a cyclic peptide of the invention as herein described for use as a medicament. According to another aspect of the present invention there is provided a method for inhibiting the interaction between VCAM-1 and/or fibronectin and the integrin receptor VLA-4 in mammals in need of such treatment which comprises administering to said mammal an effective amount of a pharmaceutical composition as described herein. In a preferred embodiment the mammal in need of treatment is suffering from multiple sclerosis or rheumatoid arthritis. In another preferred embodiment the mammal in need of treatment may be suffering from asthma or psoriasis.

According to a further aspect of the present invention there is provided a method for inhibiting the interaction between MAdCAM-1 and the integrin $\alpha 4 \beta 7$ in mammals in need of such treatment which comprises administering to said mammal an effective amount of a pharmaceutical composition as described herein or a pharmaceutically acceptable salt thereof. In a preferred embodiment the mammal in need of treatment is suffering from inflammatory bowel disease and insulin-dependent diabetes.

According to another aspect of the present invention there is provided the use of a cyclic peptide of the invention or a pharmaceutically-acceptable salt thereof in the production of a medicament for use in the treatment of a disease or medical condition mediated by the interaction between VCAM-1 or fibronectin and the integrin receptor VLA-4.

According to another aspect of the present invention there is provided the use of a cyclic peptide of the invention or a pharmaceutically-acceptable salt thereof in the production of a medicament for use in the treatment of a disease or medical condition mediated by the interaction between MAdCAM-1 and the integrin $\alpha 4 \beta 7$.

Synthetic Details

A cyclic peptide of the invention may be prepared by any process well known in the art of peptide chemistry to be applicable to the synthesis of analogous compounds. Thus, for example, a cyclic peptide of the invention may be obtained by procedures analogous to those disclosed in "Solid Phase Peptide Synthesis: A practical approach" by Atherton and Sheppard (published by IRL press at Oxford University Press, 1989). "Solid Phase Peptide Synthesis" by Stewart and Young (published by the Pierce Chemical Company, Illinois, 1984), "Principles of Peptide Synthesis" by M. Bodanszky (published by Springer-Verlag, Berlin Heidelberg, 1984), "The Practice of Peptide Synthesis" by M. Bodanszky and A. Bodanszky (published by Springer-Verlag, Berlin Heidelberg, 1984), and a series of books "Amino Acids, Peptides and Proteins" (volumes 1–26; volume 26 published in 1995) (published by the Royal Society of Chemistry, Cambridge, UK). In addition to books, a number of reviews [e.g. "Solid Phase Peptide Synthesis: a Silver Anniversary Report", G. Barany, N. Kneib-Cordonier and D. G. Mullen, International Journal of Peptide and Protein Research, 30 (1987) 705–739; "Solid Phase Peptide Synthesis Utilising 9-Fluorenylmethoxycarbonyl Amino Acids", G. B. Fields and R. L Noble, International Journal of Peptide and Protein Research, 35 (1990) 161–214] have also been published on the synthesis of peptides. Synthetic advances are also published in the proceedings of the American, European and Japanese Peptide Symposiums. Synthesis may be achieved by automated or manual means.

According to another aspect of the present invention there is provided a process for the manufacture of a cyclic peptide of the invention selected from:

(a) assembling the required linear peptide in a stepwise manner (adding one amino acid at a time) followed by selective removal of any N- and C-terminal protecting groups, cyclisation and finally deprotonation to give a cyclic peptide according to the invention and, optionally, if desired, converting the product thus obtained into a salt thereof;

(b) forming of an amide bond by coupling two peptide units, one containing a carboxylic acid group, or a reactive derivative thereof, and the other containing an amino group, such that a protected or unprotected cyclic peptide of the invention is produced, and if necessary, removing the protecting groups using process (c) below and, optionally, if desired, converting the product thus obtained into a salt thereof; and (c) removing one or more conventional peptide protecting groups from a protected cyclic peptide having a protecting group on the acid group in the side chain of Asp to give a cyclic peptide of the invention and optionally, simultaneously or subsequently, also removing any additional conventional peptide protecting groups present and, optionally, if desired, converting the product thus obtained into a salt thereof.

The above deprotection and coupling steps can be performed either on a solid support (Solid Phase Peptide Synthesis) or in solution using normal techniques used in the synthesis of organic compounds. With the exception of the solid support, all the other protecting groups, coupling reagents, deblocking reagents and purification techniques are similar in both the solid phase and solution phase peptide synthesis techniques.

For the synthesis of peptides on the solid support, a suitable resin is selected which can either provide a free carboxyl group after cleavage from the resin or a peptide derivative which can be selectively deprotected to give a C-terminal carboxyl group. The solid support may consist of polystyrene beads, polydimethylacrylamide beads, polydimethylacrylamide-polystyrene composite (Polyhipe) or polystyrene-polyoxyethylene resin (Tentagel resins). A few examples of suitable linker group containing solid supports used in the solid phase synthesis of peptides are shown below. In addition to the linkers shown, some other linkers such as hydroxycrotonoylamidomethyl (HYCRAM) can also be used. The first amino acid is then coupled to the resin by the methods described in this application for the synthesis of peptides or by using any of the coupling reagents used in the synthesis of peptides. Examples of some of the coupling reagents are also described in this application.

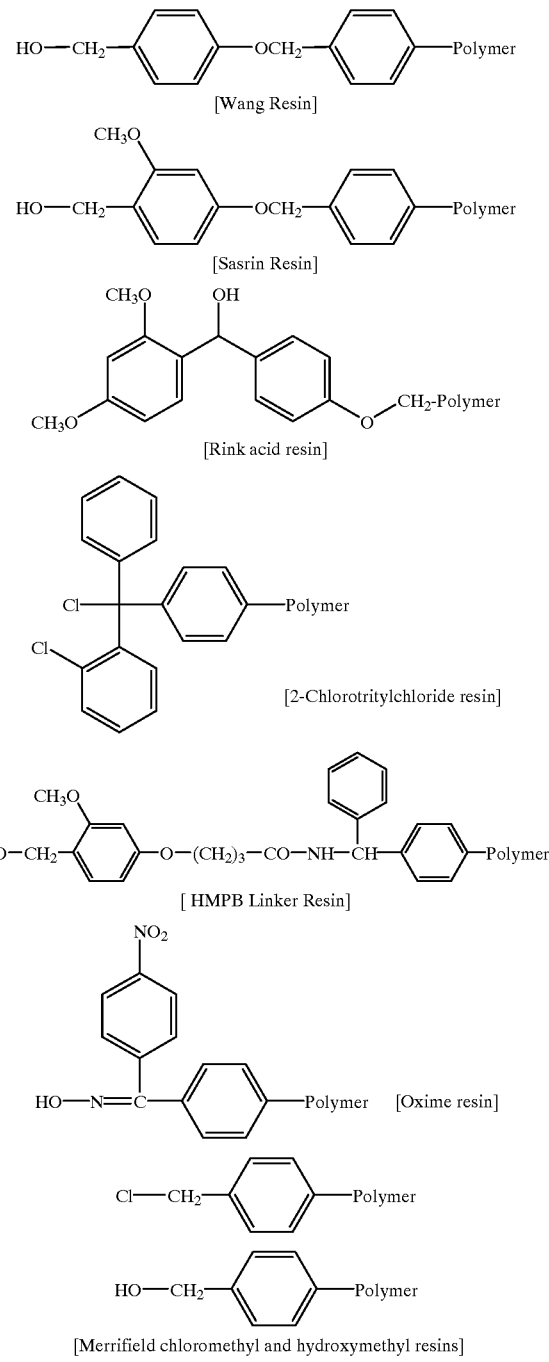

During the assembly of peptides, the amino acid functional groups not participating in the reaction are protected by various protecting groups. For example, the N-terminal and side chain amino groups can be protected by using 9-fluorenylmethoxycarbonyl (Fmoc), t-butoxycarbonyl (Boc), biphenylisopropoxycarbonyl (Bpoc), 2-[3,5-dimethoxyphenyl]propyl-2-oxycarbonyl (Ddz), adamantyloxycarbonyl (Adoc), allyloxycarbonyl (Aloc), 2,2,2-trichloroethoxycarbonyl (Troc), benzyloxycarbonyl and various substituted benzyloxycarbonyl groups. These protecting groups can be cleaved when required by the standard techniques (e.g. acid or base treatment, catalytic hydrogenolysis and Pd(0) treatment or zinc/acetic acid treatment).

Suitable protecting groups used for the protection of the α-carboxyl or the side chain carboxyl groups include various esters (e.g. methyl, ethyl, t-butyl, benzyl, nitrobenzyl, allyl and 9-fluorenylmethyl).

Suitable protecting groups used for the protection of the side chain guanidino group in the peptides containing an arginine residue include a nitro, adamantyloxycarbonyl, 4-methoxy-2,3,6-trimethylbenzenesulphonyl (Mtr), 2,2,4,6, 7-pentamethyldihydrobenzofuran-5-sulphonyl (Pbf) and 2,2,5,7,8-pentamethylchroman-6-sulphonyl (Pmc) groups. Suitable protecting groups used for the protection of the side chain imidazole group in the peptides containing a histidine residue include a trityl, tosyl, dinitrophenyl, Adoc, Boc or Fmoc group.

The protecting group cleavage reactions can be performed at temperatures between 4° C. to 40° C. (preferably at room temperature, about 25° C.). The cleavage reactions can take between 10 minutes to 24 hours.

Suitable coupling methods used for the coupling of the individual amino acids or the peptide fragments include the commonly used azide, symmetrical anhydride, mixed anhydride and various active esters and carbodiimides. In case of various carbodiimides (e.g. dicyclohexyl- or diisopropyl-carbodiimides), a number of additives [e.g. 1-hydroxybenzotriazole and N-hydroxysuccinimide) may also be added. In addition, the amino acid or fragment couplings can also be achieved by using a number of other reagents, e.g. 1H-benzotriazole-1-yl-oxy-tris-pyrrolidinophosphonium hexafluorophosphate (PyBOP), (2-(1H-benzotriazole-1 -yl)-1,1,3,3-tetramethyluronium tetrafluoroborate (TBTU) and (2-(1 H-benzotriazole-1-yl)-1,1, 3,3-tetramethyluronium hexafluorophosphate (HBTU)].

The coupling reactions can be performed at temperatures between −20° C. to 40° C. The time required for completion of the reaction may be between 10 minutes to 24 hours.

Suitable purification methods for the intermediates and final products include counter current distribution, ion exchange, gel filtration and various other chromatographic techniques including high pressure liquid chromatography (HPLC) along with many other standard techniques used in organic chemistry (e.g. solvent extraction and crystallisation).

The invention will now be illustrated by the following non-limiting examples in which:

FIG. 1 illustrates the synthesis of compound no. 1 (Table 2);

FIG. 2 illustrates the synthesis of compound no. 20 (Table 2):

FIG. 3 illustrates synthesis of compound no. 24 (Table 2);

Figure 4:
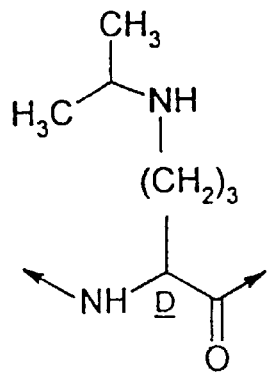
FIG. 4 illustrates the structure of D-Orn(CHMe$_2$)
Figure 5:
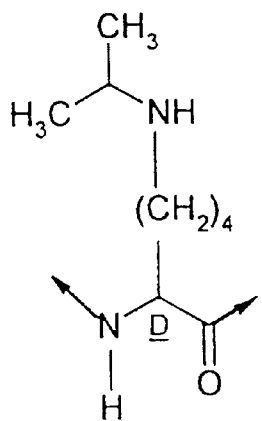
FIG. 5 illustrates the structure of D-Lys(CHMe$_2$)
Figure 6:
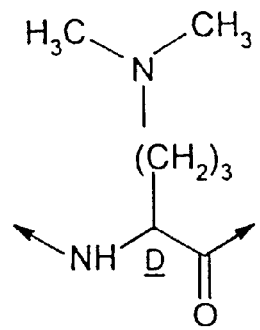
FIG. 6 illustrates the structure of D-Orn(Me$_2$)
Figure 7:
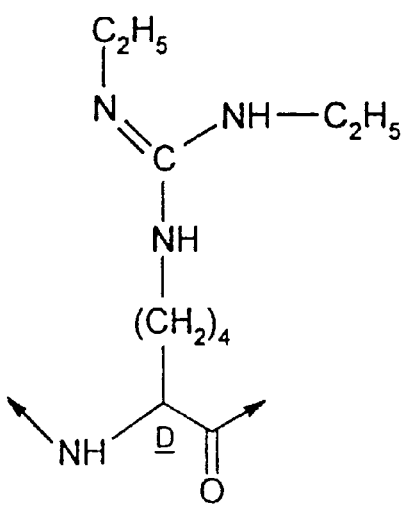
FIG. 7 illustrates the structure of D-hArg(Et)$_2$.
Figure 8:
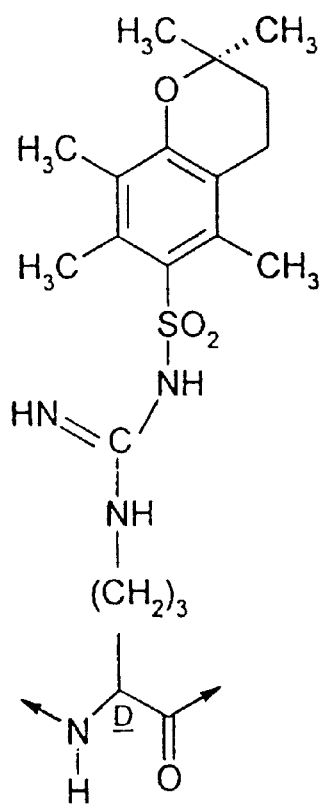
FIG. 8 illustrates the structure of D-Arg(Pmc).

In FIGS. 4 to 8 arrowed bonds indicate attachment points or direct bonds (i.e. not a —CH$_2$—group). For example, referring to D-Lys(CHMe$_2$) (FIG. 5) in compound 4 (Table 1), the arrowed bond on the nitrogen will be attached to the —C(O)—at the C-terminus of Val and the arrowed bond on the —C(O)—will be attached to the nitrogen atom at the N-terminus of D-Ala.

The following abbreviations have been used:
hArg(Et)$_2$ homo-Arg(Et)$_2$ Orn ornithine.

EXAMPLES

Syntheses of Compounds 1–38 (See Tables 1 and 2)

The cyclic peptides according to the invention are numbers 1 to 38 in tables 1 and 2. They were obtained by cyclisation of the corresponding precursor (generally linear) peptides, numbered 39 to 75 in table 1. Synthetic details for compound nos. 1, 20 and 24 are described below in detail (see FIGS. 1 to 3). In the case of other compounds, only the variations from the standard procedure are mentioned.

Example 1

Synthesis of Compound 1 (FIG. 1)

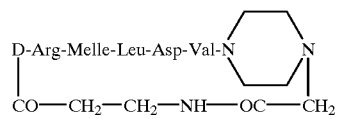

1. The cyclic peptide (FIG. 1, step 5) was prepared by the solid phase procedure using 2-chlorotritylchloride resin. After assembling the partially protected linear peptide on the resin, the peptide was cleaved from the resin and used in the subsequent steps without any purification. However, the final product was purified extensively by reverse phase high pressure liquid chromatography (HPLC) before characterisation.

1.1. Synthesis of Compound 1 (Step 1, FIG. 1)

t-Butyl bromoacetate (4.88 g, 25 mmole) in dichloromethane (50 ml) was added to a solution of t-butyl-1-piperazine carboxylate (4.65 g, 25 mmole) and triethylamine (3.5 ml, 25 mmole) in dichloromethane (30 ml). The reaction mixture was stirred overnight, filtered to remove the solids separated overnight and the filtrate evaporated to dryness. The residue was partitioned between ethyl acetate and water, the organic layer was then washed with water, dried over MgSO$_4$ and evaporated to dryness. The residue was crystallised from ether-isohexane to yield the product (5.66 g, 75%, m.p. 99–100° C.). [Elemental analysis: Found C 59.8%, H 9,6%, N 9.1%; C$_{15}$H$_{28}$N$_2$O$_4$ requires C 60.0%, H 9.4%, N 9.33%]. [Thin layer chromatography on silica gel plates showed a single spot; Rf 0.38 in ethyl acetate-isohexane (1:1) and 0.68 in methanol-chloroform (1:9)].

1.2. Synthesis of Compound 1 (Step 2, FIG. 1)

The compound described in section 1.1 (5 g, 16.6 mmole) was treated with a mixture of trifluoroacetic acid-water (95:5; 50 ml) for 1 hour. The acid was removed by evaporation in vacuum and the residual oil was triturated with ether to give a solid which was collected, washed with ether and dried over P$_2$O$_5$/KOH under vacuum (6.25 g, m.p. 177–182° C.). The solid was then dissolved in a mixture of water and acetone (1:1, 150 ml) containing potassium carbonate (6.92 g, 3 equivalents). 9-Fluorenylmethyl-N-hydroxysuccinimide (5.66 g, 16.7 mmole) in acetone (30 ml) was added over a period of 20 minutes with stirring. The pH of the solution was maintained at about 9 by the addition of M K$_2$CO$_3$ solution. After stirring overnight at room temperature, the acetone was removed by evaporation under vacuum and the aqueous solution was acidified with KHSO$_4$ solution. The product was extracted into ethyl acetate and the solution was washed with water (6 times) and with saturated NaCl solution. The organic layer was dried over MgSO$_4$ and evaporated to give an oil which solidified on trituration with isohexane and ether (yield 3.72 g, 60%). A sample was recrystallised from ethanol-ether, m.p. 179–182° C., (M+H)$^+$367.

1.3. Synthesis of Compound 1 (Steps 3 and 4, FIG. 1)

The above Fmoc-piperazine derivative (732 mg, 2 mmole) in dichloromethane (15 ml) and diisopropylethylamine (1.05 ml, 3 equivalents) were added to 2-chlorotritylchloride resin Novabiochem., 2.05 g) and the reaction mixture was shaken gently for 60 minutes. A 10% solution of diisopropylethylamine in methanol (10 ml) was added and the shaking was continued for 10 minutes. The resin was filtered off, washed successively with dichloromethane, dimethylformamide, dichloromethane, ether and dried at 50° C. in a vacuum oven (weight 2.55 g).

The above resin was placed in a reaction vessel fitted with a sintered glass disc. The following series of reactions were then carried out manually to obtain the desired peptide resin. (a) Removal of the Fmoc group with two treatments (1×5 minutes and 1×15 minutes) of 20% piperidine in dimethylformamide followed by five washes with dimethylformamide to remove excess reagents and cleavage products. (b) Acylation with Fmoc-Val (1.70 g, 5 mmole) activated with O-(benzotriazol-1-yl)-1,1,3,3 tetramethyluronium hexafluorophosphate (HBTU)(1.90 g, 5 mmole) and diisopropylethylamine (1.75 ml, 10 mmole) in dimethylformamide (8 ml) for 1 hour. The resin was again washed five times with dimethylformamide to remove excess reagents.

The above deprotection and coupling cycles were repeated using Fmoc-Asp(OBu$^t$) (2.06 g, 5 mmole), Fmoc-Leu (1.77 g, 5 mmole), Fmoc-MeIle (1.83 g, 5 mmole), Fmoc-D-Arg(Pbf) (3.76 g, 5 mmole). In the case of Fmoc-D-Arg(Pbf), the amino acid derivative was activated by O-(7-azabenzotriazol-1-yl)-1,1,3,3-tetramethyluronium hexafluorophosphate (HATU) (1.90 g, 5 mmole). One half of the resin was then deblocked and reacted with Fmoc-NH(CH$_2$)$_2$-COOH (911 mg, 3 mmole) using HBTU (1.14 g, 3 mmole) and diisopropylethylamine (1.05 ml, 6 mmole) to give the protected pentapeptide derivative attached to the chlorotrityl resin (step 3). The N-terminal Fmoc group was cleaved with 20% piperidine in dimethylformamide (1×5 minutes and 1×15 minutes) and the peptide resin was washed successively with dimethylformamide, dichloromethane and ether and dried in a vacuum oven at 50° C.

The peptide resin was treated with a mixture of acetic acid-trifluoroethanol-dichloromethane (2:2:6) (25 ml) for 1 hour. The resin was removed by filtration, and treated again with the cleavage reagent for one hour. The combined filtrates were evaporated and the residue triturated with ether to give the linear pentapeptide derivative as an acetate salt (824 mg, 0.682 mmole). The acetate salt was then converted to a hydrochloride salt by dissolving it in a mixture of water-acetonitrile (2:1, 60 ml), cooling to 0° C., adding 1.05 equivalents of IN HCl and freeze drying the contents.

1.4. Synthesis of Compound 1 (Step 5, FIG. 1)

The linear peptide was cyclised and deprotected by the procedures described below for c(MeIle-Leu-Asp-Val-D-Ala-D-Ala-D-Arg) (compound 24) in the equivalent steps to give the final cyclic peptide end product (1).

2. Synthesis of c(MePhe-Leu-Asp-Val-D-Arg-D-Arg) (Compound 20, FIG. 2)

The cyclic peptide was prepared by the solid phase procedure using 2-chlorotritylchloride resin. The synthetic details are described below. After assembling the partially protected linear peptide on the resin, the peptide was cleaved from the resin and used in the subsequent steps without any purification. However, the final product was purified extensively by reverse phase high pressure liquid chromatography (HPLC) before characterisation.

2.1. Preparation of Fmoc-Val-chlorotrityl Resin (Step 1, FIG. 2)

2-Chlorotritylchloride resin (Alexis Corporation, 1.31 mmole Cl/g; 10 g) was swollen in dichloromethane (40 ml) (dried over molecular sieve) for 5 minutes. A solution of Fmoc-Val (3.39 g, 10 mmole) and diisopropylethylamine (5.6 ml, 32 mmole) in dichloromethane (20 ml) was added and the suspension was shaken mechanically for 45 minutes. Methanol (9 ml) and diisopropylethylamine (1 ml) were added and the shaking was continued for a further five minute period. The resin was collected by filtration and washed successively with dichloromethane, dimethylformamide and dichloromethane and used immediately for the synthesis in the next step (2.2)

2.2. Preparation of D-Arg(Pbf)-D-Arg(Pbf)-MePhe-Leu-Asp(OBut)-Va -chlorotrityl Resin (Steps 2 and 3, FIG. 2)

The above Fmoc-Val resin was placed in a reaction vessel fitted with a sintered glass disc. The following series of reactions were then carried out manually to obtain the desired peptide resin.

(a) Removal of the Fmoc group with two treatments (1×5 minutes and 1×15 minutes) of 20% piperidine in dimethylformamide followed by five washes with dimethylformamide to remove excess reagents and cleavage products.

(b) Acylation with Fmoc-Asp(OBu$^t$) (6.17 g, 15 mmole), activated with O-(benzotriazol-1-yl)-1,1,3,3-tetramethyluronium hexafluorophosphate (HBTU) (5.70 g, 15 mmole) and diisopropylethylamine (5.25 ml, 30 mmole) in dimethylformamide (22 ml) for 1 hour. The resin was again washed five times with dimethylformamide to remove excess reagents.

The above deprotection and coupling cycles were repeated using Fmoc-Leu (5.29 g, 15 mmole), Fmoc-MePhe (6.01 g, 15 mmole), Fmoc-D-Arg(Pbf) (11.27 g, 15 mmole) and Fmoc-D-Arg(Pbf) (11.27 g, 15 mmole) to give Fmoc-D-Arg(Pbf)-D-Arg(Pbf)-MePhe-Leu-Asp(OBu$^t$)-Val-chlorotrityl resin. As in the case of compound 1, coupling of the Fmoc-D-Arg derivative was achieved by using O-(7-azabenzotriazol-1-yl)-1,1,3,3-tetramethyluronium hexafluorophosphate (HATU) and diisopropylethylamine. The N-terminal Fmoc group was cleaved (step 3) with 20% piperidine in dimethylformamide (1×5 minutes and 1×15 minutes) and the peptide resin, D-Arg(Pbf)-D-Arg(Pbf)-MePhe-Leu-Asp(OBut)-Val-chlorotrityl resin, was washed successively with dimethylformamide and dichloromethane.

23. Preparation of D-Arg(Pbf)-D-Arg(Pbf)-MePhe-Leu-Asp(OBu$^t$)-Val, HCl. (Step 4, FIG. 2)

The peptide resin, D-Arg(Pbf)-D-Arg(Pbf)-MePhe-Leu-Asp(OBu$^t$)-Val-chlorotrityl resin, was suspended in a mixture of acetic acid-trifluoroethanol-dichloromethane (2:2:6) (100 ml) for 1 hour. The resin was removed by filtration and retreated with the same mixture for a further one hour. The combined filtrates were evaporated and the residue triturated with ether to give D-Arg(Pbf)-D-Arg(Pbf)-MePhe-Leu-Asp(OBu$^t$)-Val as an acetate salt (11.66 g). The acetate salt was then converted to a hydrochloride salt by dissolving it in a mixture of water-acetonitrile (2:1, 350 ml), cooling to 0° C., adding 1.05 equivalents of 1N HCl and freeze drying the contents (weight 11.5 g).

2.4. Preparation of c(D-Arg(Pbf)-D-Arg(Pbf)-MePhe-Leu-Asp(OBut)-Val) (Step 5, FIG. 2)

The above linear peptide hydrochloride, D-Arg(Pbf)-D-Arg(Pbf)-MePhe-Leu-Asp(OBu$^t$)-Val (HCl), (11.5 g, 8.1 mmole) was dissolved in dimethylformamide (8000 ml) and O-7-azabenzotriazol-1-yl)-1,1,3,3-tetramethyluronium hexafluorophosphate (HATU) (4.62 g, 12.15 mmole), and diisopropylethylamine (5.67 ml, 32.4 mmole) were added to the solution. The cyclisation reaction was monitored by analytical HPLC. On completion of the reaction (2 hours at room temperature), the reaction mixture was evaporated to dryness in vacuum. The residue was triturated with 10% aqueous sodium bicarbonate solution. The solid was collected and washed with 10% sodium bicarbonate, water, 10% potassium hydrogen sulphate solution and finally with water. The solid was dried over $P_2O_5$ at 45° C. in a vacuum oven [retention time 24.80 minutes on a Vydac 218TP54 column using a gradient of acetonitrile-water containing 0.1% trifluoroacetic acid (40–80%) over a period of 30 minutes at a flow rate of 1.0 ml/minute] and was used in the next step without any purification.

2.5. Preparation of c(MePhe-Leu-Asp-Val-D-Arg-D-Arg) [Compound 20] (Step 6, FIG. 2)

The above protected cyclic peptide, c(D)-Arg(Pbf)-D-Arg(Pbf)-MePhe-Leu-Asp(OBu$^t$)-Val), was treated for 90 minutes with a mixture of trifluoroacetic acid-water (95:5, 80 ml) and triisopropylsilane (3 ml) to remove the arginine and aspartic acid side chain protecting groups. The reaction mixture was evaporation to a small volume and partitioned between water and ether. The aqueous layer was washed 4 times with ether and freeze dried to give 10.9 g crude product. The crude product was purified by preparative reverse phase HPLC on a Vydac $C_{18}$ 218TP1015100 column (4 inch×25 cm) using a gradient of acetonitrile-water containing 0.1% trifluoroacetic acid (15–35%) over a period of 80 minutes at a flow rate of 180.0 ml/minute. The product-containing fractions were combined and freeze dried to give the purified cyclic peptide (3.63 g). The peptide was characterised by amino acid analysis and mass spectroscopy (table 2).

3. Synthesis of c(D-Arg-MeIle-Leu-Asp-Val-D-Ala-D-Ala) (Compound 24, FIG. 3)

The cyclic peptide was prepared by the solid phase procedure using 2-chlorotritylchloride resin. After assembling the partially protected linear peptide on the resin, the peptide was cleaved from the resin and used in the subsequent steps without any purification. However, the final product was purified extensively by reverse phase high pressure liquid chromatography (HPLC) before characterisation.

3.1. Preparation of Fmoc-D-Ala-chlorotrityl Resin (Step 1, FIG. 3)

2-Chlorotritylchloride resin (Nova Biochem.; 1.35 mmole Cl/g; 1 g) was swollen in dichloromethane (10 ml) (dried over molecular sieve) for 5 minutes. A solution of Fmoc-D-Ala (311 mg, 1 mmole) and diisopropylethylamine (525 μl, 3 mmole) in dichloromethane (8 ml) was added and the suspension was shaken mechanically for 45 minutes. Methanol (9 ml) and diisopropylethylamine (1 ml) were added and the shaking was continued for a further five minute period. The resin was collected by filtration and washed successively with dichloromethane, dimethylformamide, dichloromethane, isopropanol and ether, and finally dried at 50° C. in a vacuum oven (weight 1.51 g)

3.2. Preparation of D-Arg(Pmc)-MeIle-Leu-Asp(OBut)-Val-D-Ala-D-Ala-chlorotrityl Resin (Steps 2 and 3, FIG. 3)

The above Fmoc-D-Ala resin was placed in a reaction vessel fitted with a sintered glass disc. The following series of reactions were then carried out manually to obtain the desired peptide resin.

(a) Removal of the Fmoc group with two treatments (1×5 minutes and 1×15 minutes) of 20% piperidine in dimethylformamide followed by five washes with dimethylformamide to remove excess reagents and cleavage products.

(b) Acylation with Fmoc-D-Ala (622 mg, 2 mmole), activated with O-(benzotriazol-1-yl)-1,1,3,3-tetramethyluronium hexafluorophosphate (HBTU) (760 mg, 2 mmole) and diisopropylethylamine (700 μl, 4 mmole) in dimethylformamide (3 ml) for 1 hour. The resin was again washed five times with dimethylformamide to remove excess reagents.

The above deprotection and coupling cycles were repeated using Fmoc-Val (678 mg, 2 mmole), Fmoc-Asp (OBu$^t$) (822 mg, 2 mmole), Fmoc-Leu (700 mg, 2 mmole), Fmoc-MeIle (734 mg, 2 mmole) and Fmoc-D-Arg(Pmc) (1.40 g, 2 mmole) to give Fmoc-D-Arg(Pmc)-MeIle-Leu-Asp(OBu$^t$)-Val-D-Ala-D-Ala-chlorotrityl resin. As in the case of compound 1, coupling of the Fmoc-D-Arg derivative was achieved by using O-(7-azabenzotriazol-1-yl)-1,1,3,3-tetramethyluronium hexafluorophosphate (HATU) and diisopropylethylamine. The N-terminal Fmoc group was cleaved (step 3) with 20% piperidine in dimethylformamide (1×5 minutes and 1×15 minutes) and the peptide resin, D-Arg(Pmc)-MeIle-Leu-Asp(OBut)-Val-D-Ala-D-Ala-chlorotrityl resin, was washed successively with dimethylformamide, dichloromethane and ether and dried in a vacuum oven at 50° C. (weight 2.5 g).

3.3. Preparation of D-Arg(Pmc)-MeIle-Leu-Asp(OBu$^t$)-Val-D-Ala-D-Ala (HCl) (Step 4, FIG. 3)

The peptide resin, D-Arg(Pmc)-MeIle-Leu-Asp(OBut)-Val-D-Ala-D-Ala-chlorotrityl resin, was suspended in a mixture of-acetic acid-trifluoroethanol-dichloromethane (2:2:6) (25 ml) for 1 hour. The resin was removed by filtration and retreated with the same mixture for a further one hour. The combined filtrates were evaporated and the residue triturated with ether to give D-Arg(Pmc)-MeIle-Leu-Asp(OBut)-Val-D-Ala-D-Ala as an acetate salt (1.18 g). The acetate salt was then converted to a hydrochloride salt by dissolving it in a mixture of water-acetonitrile (2:1, 60 ml), cooling to 0° C., adding 1.05 equivalents of 1N HCl and freeze drying the contents.

3.4. Preparation of c(D-Arg(Pmc)-MeIle-Leu-Asp(OBu$^t$)-Val-D-Ala-D-Ala) (Step 5, FIG. 3)

The above linear peptide hydrochloride, D-Arg(Pmc)-MeIle-eu-Asp(OBu$^t$)-Val-D-Ala-D-Ala (HCl), (1.18 g, 1.02 mmole) was dissolved in dimethylformamide (1000 ml) and O-(benzotriazol-1-yl)-1,1,3,3-tetramethyluronium hexafluorophosphate (HBTU) (395 mg, 1.02 mmole), and diisopropylethylamine (545 μl, 3.1 mmole) were added to the solution. The cyclisation reaction was monitored by analytical HPLC. On completion of the reaction (2 hours at room temperature), the reaction mixture was evaporated to dryness in vacuum. The residue was partitioned between ethyl acetate and water. The organic layer was then washed successively with 1M citric acid, saturated sodium chloride, 10% sodium bicarbonate, and saturated sodium chloride, dried over magnesium sulphate and evaporated to dryness in vacuum. The product was collected [retention time 27.06 minutes on a Vydac 218TP54 column using a gradient of acetonitrile-water containing 0.1% trifluoroacetic acid (20–80%) over a period of 30 minutes at a flow rate of 1.0 ml/minute] and was used in the next step without any purification.

3.5. Preparation of c(D-Ala-D-Ala-D-Arg-MeIle-Leu-Asp-Val) [Compound 24] (Step 6, FIG. 3)

The above protected cyclic peptide, c(D-Ala-D-Ala-D-Arg(Pmc)-MeIle-Leu-Asp(OBu$^t$)-Val), was treated for 4 hours with a mixture of trifluoroacetic acid-water (95:5, 30 ml) and triisopropylsilane (1 ml) to remove the arginine and aspartic acid side chain protecting groups. Evaporation to a small volume, followed by trituration with ether yielded the crude cyclic peptide (575 mg). The crude product was purified by preparative reverse phase HPLC on a Deltapak $C_{18}$ column (30×30 mm) using a gradient of acetonitrfle-water containing 0.1I% trifluoroacetic acid (10–30%/) over a period of 80 minutes at a flow rate of 30.0 ml/minute. The product-containing fractions were combined and freeze dried to give the purified cyclic peptide (353 mg). The peptide [single peak on HPLC, retention time 21.19 minutes on a Vydac 218TP54 column using a gradient of acetonitrile-water containing 0.1% trifluoroacetic acid (10 –40%) over a period of 30 minutes at a flow rate of 1.0 ml/minute] was characterised by amino acid analysis and mass spectroscopy (table 2).

4. Synthesis of Compound 2

Compound 2 was synthesised by the route used for compound 1 (shown in FIG. 1) except that γ-aminobutyric acid was used in place of β-alanine.

5. Syntheses of Compounds 3 to 5

The above cyclic peptides were prepared by reacting the cyclic peptide c(MeIle-Leu-Asp-Val-D-Orn-D-Orm) or c(MeIle-Leu-Asp-Val-D-Lys-D-Ala) with the required aldehyde or ketone and sodium cyanoboreohydride. For example, compound 3 was prepared by dissolving the cyclic peptide c(MeIle-Leu-Asp-Val-D-Orn-D-Orn) (100 μmole) in dry acetone (2 ml) and reacting with sodium cyanoborohydride (IO equivalents). After an hour, the reaction mixture was evaporated to dryness and the residue, dissolved in water (5 ml), was acidified with acetic acid and evaporated under high vacuum. The crude peptide was purified by HPLC.

The parent cyclic peptides c(MeIle-Leu-Asp-Val-D-Orn-D-Orn) and c(MeIle-Leu-Asp-Val-D-Lys-D-Ala) were synthesised by the route described for compound 24 in FIG. 3.

6. Syntheses of Compounds 6 to 8

The linear peptides, D-hArg(Et)$_2$-MeIle-Leu-Asp(OBut)-Val-D-Ala, D-hArg(Et)$_2$-MeIle-Leu-Asp(OBut)-Val-D-Phe and D-hArg(Et)$_2$-D-hArg(Et)$_2$-MeIle-Leu-Asp(OBut)-Val, required for compounds 6 to 8 were obtained by the procedures described for compound 24. The synthesis was started from the required C-terminal amino acid, i.e. D-Ala for compound 6, D-Phe for compound 7 and Val for compound 8). The synthetic routes to Boc-D-hArg(Et)$_2$ have been reported earlier in the literature [H.B. Arzeno et al., Synthetic Communications, 20 (1990) 3433–3437; J. J. Nestor, Jr. et al., Journal of Medicinal Chemistry, 35 (1992) 3942–3948]. This derivative was converted to Fmoc-D-hArg(Et)$_2$ by the standard procedures and used in the syntheses of the above linear peptides. Compounds 6 to 8 were then obtained from the corresponding linear peptides by the cyclisation methods described for compound 24 in FIG. 3.

7. Syntheses of Compounds 9 to 19

Cyclic peptides 9 to 19 were synthesised by the procedures similar to that described for compound 24. As mentioned in table 1, all the linear peptides were synthesised on the chlorotrityl resin starting from Fmoc-Valine.

8. Syntheses of compounds 21 to 23 and 25 to 32

Cyclic peptides 21 to 23 and 25 to 32 were synthesised by the procedures similar to that described for compound 20. As mentioned in table 1, all the linear peptides were synthesised on the chlorotrityl resin starting from Fmoc-Valine.

9. Syntheses of Compounds 33 to 35

Cyclic peptides 33 to 35 were synthesised by the procedures similar to that described for compound 20. However, as shown in table 1, the three linear peptides were synthesised on the chlorotrityl resin starting from Fmoc-NH(CH$_2$)$_5$-COOH, Fmoc-NH(CH$_2$)$_2$—S—CH$_2$—COOH or Fmoc-NH(CH$_2$)$_2$—S—(CH$_2$)$_2$—COOH derivatives in place of Fmoc-Valine.

Unlike aminohexanoic acid which is commercially available, the other two sulphur containing amino acid derivatives were synthesised by the following procedures. Fmoc-NH(CH$_2$)$_2$—S—CH$_2$—COOH (used above) was obtained from 2-aminoethanethiol and 2-bromoacetic acid. 2-Aminoethanethiol hydrochloride (5.68 g, 50 mmole) was dissolved in water (200 ml) and sodium hydrogen carbonate (25.2 g, 300 mmole) was added to it. 2-Bromoacetic acid (6.95 g, 50 mmole) dissolved in acetonitrile (100 ml) was added in portions over 30 minutes to the stirred solution prepared above. After 1 hour at room temperature, a solution of 9-fluorenylmethyl-N-hydroxysuccinimide (Fmoc-OSu) (16.85 g. 50 mmole) in acetonitrile (150 ml) was added and the stirring was continued for 16 hours. The slightly turbid solution was evaporated to remove-most of-the acetonitrile and the remaining aqueous solution was extracted with ethyl acetate (3×50 ml) and acidified (pH 2) by the addition of hydrochloric acid. The white solid wHs collected, washed with water and dried in vacuo at 45° C. Yield 17 g (95%), (M+H)$^+$ 358.0.

Fmoc-NH(CH$_2$)$_2$—S—(CH$_2$)$_2$—COOH was obtained by the procedure described above for Fmoc-NH(CH$_2$)$_2$—S—CH$_2$—COOH by using 3-bromopropionic acid and 2-aminoethanethiol. (M+H)$^+$ 372.

10. Syntheses of Compounds 36 to 38

Cyclic peptides 36 to 38 were synthesised by the procedures similar to that described for compound 20. As mentioned in table 1, all the linear peptides, except compound 61, were synthesised on the chlorotrityl resin starting from Fmoc-Valine. As shown in FIG. 2, compound 61 was prepared starting from Fmoc-Ala. The sulphur containing amino acid residue, —NH(CH$_2$)$_2$—S—CH$_2$—CO—, was incorporated by using Fmoc-NH(CH$_2$)$_2$—S—CH$_2$—COOH at the appropriate stage in the synthesis of the linear peptides.

Example 2

In Vitro and In Vivo Assays

The following abbreviations and sources of materials are used in this example. MOLT-4 cells—lymphocytic T cell line (ATCC derived) Fibronectin —Made according to the methods described in E.Nengvall, E. Ruoslahti, Int. J. Cancer, 1977, 20, pages 1–5 and J. Forsyth et al, Methods in Enzymology, 1992, 215, pages 311–316) or reagent grade human fibronectin. The later was purified from human plasma by gelatin-sepharose affinity chromatography. Source: Bio Products Elstree UK. Product No. 9136. A review article on fibronectins is Fibronectins—Adhesive Glycoproteins of Cell Surface and Blood, K. M. Yamada and K. Olden, Nature, 275 (1978) 179–184. rsVCAM-1—(Reference source: Biochem Biophys Res Comm 1991 178 N3; 1498–1504). VCAM-1 is a cell surface glycoprotein produced by the vascular endothelium, as well as on macrophage-like and dandritic cell types, in response to certain inflammatory stimuli. VCAM-1 interacts with the integrin VLA-4 present on mononuclear leukocytes. The cDNA for VCAM-1 was isolated by screening a cDNA library from IL-1β-activated human endothelial cells. Large quantities of the Stein were expressed in insect cells using a baculovirus expression system. VCAM-1 expressing cells were shown to bind specifically to a variety of VLA-4 expressing cell lines (Jurkat, THP-1, U937). Another reference on VCAM-1 is Expression and Functional Characterisation of Recombinant Human Vascular Cell Adhesion Molecule-1 (VCAM-1) Synthesised by Baculovirus-Infected Insect Cells, J. K. Stoltenborg, R. A. Straney, R. J. Tritch, W. M. Mackin and H. J. George, Protein Expression and Purification, 4 (1993) 585–593.

RPMI 1640—Cell media. Source Gibco BRL (Life technologies; Cat No 31870-025).

FCS—Foetal calf serum. Source Advanced protein products (West Midlands UK) Cat No AS-302-50.

BCECF-AM—2', 7'-bis (2 carboxyethyl)-5-($\epsilon$6)-carboxyfluoroscein acetoxymethyl ester). source: Molecular Probes Inc USA; Cat No B-1 150.

CHO DG44—Chinese hamster ovary cell line (ATCC derived; Reference: Som Cell Mol Gen 1986; 12; 555–666)

DMEM—Dulbecco's modified eagle medium. Source Gibco BRL (Life technologies; Cat No 41966-029.

Antibiotic—Penicillin-streptomycin. Source Gibco BRL (Life Technologies; Cat No 15070-022).

Fluorskan™—is a fluorimeter.

HUVEC—Human umbilical vein endothelial cells. Primary cultures prepared from tissue samples. (Reference: J Clin Invest. 1973 52; 2745–2747. Recombinant human TNFAα—Tumor necrosis factor Alzet osmotic minipump—Subcutaneous implanted micro osmotic pump, Alza Corporation Palo Alto, Calif. In the following assays and models references to compound (s) refers to cyclic peptide(s) of the present invention.

2.1 Cell/Immobilised Ligand Assays

2.1.1 MOLT4 cell/Fibronectin-VCAM-1 Adhesion Assay.

The MOLT4 cell/Fibronectin-VCAM-1 adhesion assay was used to investigate the interaction of the integrin VLA4 (Very Late Antigen, α4/β1) expressed on the MOLT-4 cell membrane with fibronectin or recombinant soluble VCAM-1 (rsVCAM-1). Fibronectin or rsVCAM-1 were coated overnight at 4° C. onto polystyrene 96-well microtitre plates at concentrations of 20µg/ml and 1 µg/ml respectively. Following this, a concentrated BSA solution (10 mg/ml) was added to block non-specific binding sites. After aspiration of these solutions, equal volumes of compound and MOLT-4 cell suspension (1×10E6 cells/ml) were added. Adhesion took place during a 2 hour incubation at 37° C., non or loosely adherent cells were removed by gentle agitation followed by vacuum aspiration. Quantitation of the remaining adherent cells was by means of a colorimetric assay of acid phosphatase activity, which was read on a spectrophotometer. Compounds which inhibited adhesion gave a lower absorbance reading. Standard, control and test conditions were assayed in triplicate. Percentage inhibition was calculated with respect to total (no inhibitor) and non-specific (no fibronectin) standards on each plate.

2.1.2 JY cell/MAdCAM-1 Adhesion Assay

The JY cell (human B lymphoblastoid)/MAdCAM-1 adhesion assay was used to investigate the interaction of the integrin α4β7 expressed on the JY cell membrane with recombinant soluble MAdCAM-1. MAdCAM-1 was coated onto polystyrene 96-well microtitre plates for 1 hour at a concentration of 10 µg/ml. Following this, a concentrated BSA solution (10 mg/ml) was added to block non-specific binding sites. After aspiration of these solutions, equal volumes of compound and JY cell suspension (1×10E6 cells/ml) were added. The assay contained manganese at a final concentration of 0.2 mM to activate the α4β7 on the JY cells. Adhesion took place during a 20 minute incubation at 37° C. Non or loosely adherent cells were removed by gentle agitation followed by vacuum aspiration. Adherent cells were then fixed with 5% glutaraldehyde for 20 minutes and stained for 20 minutes with a 0.1% solution of crystal violet. The crystal violet was solublised by adding 10% acetic acid and the number of adherent cells quantitated by measuring absorbance at 405 nm on a spectrophotometer. Compounds which inhibited adhesion resulted in a lower absorbance reading. Standard, control and test conditions were assayed in quintuplicate. Percentage inhibition was calculated with respect to total (no inhibitor) and non-specific (no MAdCAM-1) standards on each plate.

2.2 Cell-Cell Assays

2.2.1. VCAM-1 CHO cells

MOLT4 cells (RPMI 1640 supplemented with 5% FCS and 2mM L-Glutamine) were labelled with the fluorescent dye BCECF-AM (30 µg/ml per 3×10E6 cells). CHO DG44 transfected with full length VCAM-1 cDNA were selected for VCAM-1 expression by FACS analysis and grown to confluence in 96 well tissue culture plates. Prior to use in the adhesion assay CHO DG44 cells were washed three times (DMEM supplemented with 5% FCS, 2mM L-Glutamine and 2% antibiotic). MOLT-4 (10E5 cell/well) cells were over laid on the VCAM-1 expressing CHO cells and incubated for 30 minutes at 37° C., 5% $CO_2$. The non-adherent cells were removed by washing the plate three times (RPMI 1640 supplemented with 5% FCS and 2mM L-Glutamine) following which the plates were blotted dry on tissue paper. 100 µl of 2% Triton X-100 was added to each well and the plates read using a Fluoroskan (excitation=485 nM, emission=538 nM). Compounds were dissolved in appropriate solvents and added to the MOLT-4 cells prior to addition to HUVEC cultures. is Inhibition of adhesion was calculated by comparing level of adhesion (fluorescence) of control vehicle treated cells with compound treated cells.

2.2.2 Human Umbilical Vein Endothelial Cells.

MOLT4 cells (RPMI 1640 supplemented with 5% FCS and 2mM L-Glutamine) were labelled with the fluorescent dye BCECF-AM (30 µg/ml per 3×10E6 cells). Primary HUVEC was grown to confluence in 96 well tissue culture plates and incubated for 18 hours with 2 U/ml recombinant human TNFα. Prior to use in the adhesion assay the primary HUVEC monolayers were washed (M199 supplemented with 5% FCS, 2mM L-Glutamine and 2% antibiotic). MOLT-4 (10E5cell/well) cells were overlaid on the primary HUVEC and incubated for 30 minutes at 37° C., 5% $CO_2$. The non-adherent cells were removed by washing the plate three times (RPMI 1640 supplemented with 5% FCS and 2mM L-Glutamine) and dried by blotting on tissue paper. 100 μl of 2% Triton X-100 was added to each well and the plates read using a Fluoroskan (excitation=485 nM, emission=538 nM). Compounds were dissolved in appropriate solvents and added to the MOLT-4 cells prior to addition to HUVEC cultures. Inhibition of adhesion was calculated comparing level of adhesion (fluorescence) of control vehicle treated cells with compound treated cells.

2.3 In Vivo Contact Hypersensitivity Response

Balb/C male mice (20–25g) are sensiti'sed with oxazolone (50 μl of 0.24% in acetonelolive oil) by topical application to the shaved skin area of the back. Seven days later the mice are challenged by topical application of oxazolone (25 μl of 0.25% in acetone/olive oil) to the surface of the ear. Swelling of the ear develops over a 24 hour period following which ear thickness is measured and compared to the pre-challenge thickness, the percentage increase in ear thickness is calculated. Compounds are delivered by continuous infusion at doses within the range from 10 mg/kg/day to 0.001 mg/kg/day from subcutaneous Alzet osmotic minipumps which are implanted 24 hours prior to the oxazolone challenge. Inhibition of the inflammatory response is calculated comparing vehicle treated animals and compound treated groups (n=6 animals per group).

2.4 In Vivo Ovalbumin Delayed Type Hypersensitivity Model.

Balb/C female mice (20–25 g) were immunised on the flank with an emulsion of ovalbumin (Sigma; 0.1 ml subcutaneous injection of 2 mg/ml solution mixed (1:1) with complete Freunds adjuvant; Difco). Seven days later the mice were challenged by subplantar injection of ovalbumin (30 μl of 1% heat aggregated ovalbumin in saline) into the left hind foot pad. Swelling of the foot developed over a 24 hour period following which foot pad thickness was measured and compared to the pre-challenge thickness. The percentage increase in foot pad thickness was calculated. Compounds were delivered by continuous infusion at doses within the range from 10 mg/kg/day to 0.001 mg/kg/day from subcutaneous Alzet osmotic minipumps which were implanted 24 hours prior to the ovalbumin challenge. Inhibition of the inflammatory response was calculated comparing vehicle treated animals and compound treated groups (n=5 animals per group).

2.5 In Vivo Antigen Induced Arthritis Model.

Mice are inmnunised and boosted 7 days later with a combination of 100 μg methylated BSA in complete Freund's adjuvant (s.c.) followed by an intraperitoneal injection of bordetella pertussis organisms. Two weeks after boost animals are challenged with 100 μg methylated-bovine serum albumin (BSA) intra-articularly and the degree of inflammation/arthritis determined by measuring knee joint swelling, histology and changes in acute phase proteins. Compounds are delivered by continuous infusion at a dose rate ranging from 30 mg/kg/day to 0.001 mg/kg/day from subcutaneous Alzet osmotic minipumps which are implanted 24 hours prior to the challenge. The degree of inflammation/arthritis is compared with the control animals and contralateral knee.

2.6 Experimental Autoimmune Encephalomyelitis Model.

Disease was induced by s.c. injection of a mixture of spinal cord homogenate, myelin basic protein (MBP) or encephalogenic peptides with complete Freund's adjuvant (CFA), coupled with an i.p. injection of pertussis toxin. For acute disease, pertussis injection was repeated 2 days after immunisation. For chronic disease, pertussis was omitted and mice received two injections of antigen in CFA, with an interval of 7 days. Disease was assessed by clinical scoring supported by histology. Compounds were dosed by continuous infusion at doses within the range from 10 mg/kg/day to 0.001 mg/kg/day from subcutaneous Alzet osmotic minipumps which were implanted 24 hours prior to challenge. Symptoms were compared with the control animals.

2.7 Mouse Bronchiolar Lavage Eosinophilia Model

Male C57BL/6J mice (20–25 g) were sensitised by i.p. injection of 0.1 ml saline containing 100 μg ovalbumin and 2.5 mg aluminium hydroxide three times at 4 to 5 day intervals. Ten to fourteen days after the last sensitising injection the animals were placed in a Perspex chamber and exposed (0.5 to 1 h) to aerosolised ovalbumin dissolved in saline (up to 15 mg/ml) delivered from a DeVilbiss Aerosonic nebuliser into a stream of air entering the chamber at approximately 3 l/min. Mice were exposed to aerosolised ovalbumin for 2 to 4 periods over 3 to 4 days and the day after the final exposure were killed by overdose of sodium barbitone. The trachea of each mouse was exposed, cannulated with a ball-tipped needle and bronchioalveolar lavage performed with 4×1 ml saline. The cells in the pooled lavage fluid were coated onto a glass microscope slide and fixed and stained with Leukostat stain. Differential cell counts were performed by counting a minimum of 200 leukocytes and the percentage of eosinophils was calculated. Test compounds were delivered at doses within the range from 10 mg/kg/day to 0.001 mg/kg/day from subcutaneous Alzet osmotic minipumps implanted 24 h before aerosolised ovalbumin challenge. Inhibition of eosinophilia was calculated by comparing mice dosed with vehicle or compound (n=5–10 per group).

2.8 Collagen-Induced Arthritis Model

DBA/1 male mice (ex Harlan/Olac U.K.)-were immunised with 0.1 ml of a mixture of equal parts of bovine collagen type II in 0.05 M acetic acid at 2 mg/ml and complete Freunds adjuvant (Sigma). This mixture was injected at the base of the tail. Twenty days later compounds or vehicles were delivered by continuous infusion at doses within the range from 10 mg/kg/day to 3 mg/kg/day from subcutaneous Alzet osmotic minipumps. On the following day, each animal received an intra-peritoneal booster injection of 0.1 ml of collagen type II in acetic acid. The degree of arthritis of vehicle treated and compound treated animals was compared.

TABLE 1

Synthesis and purification of cyclic peptides.

| NO: | Precursor | NO: | End Product Cyclic Peptide | High Pressure Liquid Chromatography (HPLC) (Gradient system and time) |
|---|---|---|---|---|
| 39 | MeIle-Leu-Asp(OBut)-Val-N⟨piperidine⟩ HOOC—CH₂ D-Arg(Pbf)-CO(CH₂)₃—NH₂ | 1 | D-Arg-MeIle-Leu-Asp-Val-N⟨piperidine ring with CO—CH₂—CH₂—NH—OC—CH₂⟩ | Deltapak column 15–30% (80 min.) |
| 40 | MeIle-Leu-Asp(OBut)-Val-N⟨piperidine⟩ HOOC—CH₂ D-Arg(Pbf)-CO(CH₂)₂—NH₂ | 2 | D-Arg-MeIle-Leu-Asp-Val-N⟨piperidine ring with CO—CH₂—CH₂—NH—OC—CH₂⟩ | Deltapak column 10–30% (80 min.) |
| 41 | c(MeIle-Leu-Asp-Val-D-Orn-D-Orn) | 3 | c(MeIle-Leu-Asp-Val-D-Orn(CHMe₂)-D-Orn(CHMe₂)) | 10–40% (70 min.) (12 ml/min.) |
| 42 | c(MeIle-Leu-Asp-Val-D-Lys-D-Ala) | 4 | c(MeIle-Leu-Asp-Val-D-Lys(CHMe₂)-D-Ala) | Dynamax column 10–50% (60 min.) |
| 41 | c(MeIle-Leu-Asp-Val-D-Orn-D-Orn) | 5 | c(MeIle-Leu-Asp-Val-D-Orn(Me₂)-D-Orn(Me₂)) | 15–45% (65 min.) (15 ml/min.) |
| 43 | D-hArg(Et)₂-MeIle-Leu-Asp(OBut)-Val-D-Ala | 6 | c(MeIle-Leu-Asp-Val-D-Ala-D-hArg(Et)₂) | 10–50% (60 min.) |
| 44 | D-hArg(Et)₂-MeIle-Leu-Asp(OBut)-Val-D-Phe | 7 | c(MeIle-Leu-Asp-Val-D-Phe-D-hArg(Et)₂) | 10–50% (60 min.) |
| 45 | D-hArg(Et)₂-D-hArg(Et)₂-MeIle-Leu-Asp(OBut)-Val | 8 | c(MeIle-Leu-Asp-Val-D-hArg(Et)₂-D-hArg(Et)₂) | 10–50% (60 min.) |
| 46 | D-Lys(Boc)-D-His(Trt)-MeIle-Leu-Asp(OBut)-Val | 9 | c(MeIle-Leu-Asp-Val-D-Lys-D-His) | 10–30% (60 min.) |
| 47 | D-Arg(Pmc)-D-Lys(Boc)-MeIle-Leu-Asp(OBut)-Val | 10 | c(MeIle-Leu-Asp-Val-D-Arg(Pmc)-D-Lys) | 10–60% (60 min.) |
| 48 | D-Lys(Boc)-D-Arg(Pmc)-MeIle-Leu-Asp(OBut)-Val | 11 | c(MeIle-Leu-Asp-Val-D-Lys-D-Arg) | 10–30% (60 min.) |
| 49 | D-Ala-D-Lys(Boc)-MePhe-Leu-Asp(OBut)-Val | 12 | c(MePhe-Leu-Asp-Val-D-Ala-D-Lys) | 10–40% (60 min.) |
| 50 | D-Arg(Pmc)-D-Lys(Boc)-MeIle-Leu-Asp(OBut)-Val | 13 | c(MeIle-Leu-Asp-Val-D-Arg-D-Lys) | 10–30% (60 min.) |
| 51 | D-Ala-D-Ala-Lys(Boc)-Leu-Asp(OBut)-Val | 14 | c(Lys-Leu-Asp-Val-D-Ala-D-Ala) | 10–20% (60 min.) |
| 52 | D-Ala-D-Ala-Arg(Pmc)-Leu-Asp(OBut)-Val | 15 | c(Arg-Leu-Asp-Val-D-Ala-D-Ala) | 5–20% (60 min.) |
| 53 | D-Ala-D-Lys(Boc)-D-Phe-Leu-Asp(OBut)-Val | 16 | c(D-Phe-Leu-Asp-Val-D-Ala-D-Lys) | 10–30% (60 min.) |
| 54 | D-Ala-D-Ala-MePhe-Leu-Asp(OBut)-Val | 17 | c(Mephe-Leu-Asp-Val-D-Ala-D-Ala) | 10–50% (60 min.) |
| 55 | D-Ala-D-Ala-D-Phe-Leu-Asp(OBut)-Val | 18 | c(D-Phe-Leu-Asp-Val-D-Ala-D-Ala) | 20–40% (60 min.) |
| 56 | D-Ala-D-Lys(Boc)-D-Met-Leu-Asp(OBut)-Val | 19 | c(D-Met-Leu-Asp-Val-D-Ala-D-Lys) | 5–20% (60 min.) |
| 57 | D-Arg(Pbf)-D-Arg(Pbf)-MePhe-Leu-Asp(OBut)-Val | 20 | c(MePhe-Leu-Asp-Val-D-Arg-D-Arg) | 15–30% (100 min.) |
| 58 | D-Arg(Pbf)-D-His(Trt)-MePhe-Leu-Asp(OBut)-Val | 21 | c(MePhe-Leu-Asp-Val-D-Arg-D-His) | 15–30% (100 min.) |
| 59 | D-Trp-D-Arg(Pbf)-MePhe-Leu-Asp(OBut)-Val | 22 | c(MePhe-Leu-Asp-Val-D-Trp-D-Arg) | 25–35% (90 min.) |
| 60 | D-Arg(Pmc)-D-Ala-D-Arg(Pmc)-MeIle-MePhe-Leu-Asp(OBut)-Val | 23 | c(MePhe-Leu-Asp-Val-D-Arg-D-Ala-D-Arg) | 5–30% (60 min.) |
| 61 | D-Arg(Pmc)-MeIle-Leu-Asp(OBut)-Val-D-Ala-D-Ala | 24 | c(MeIle-Leu-Asp-Val-D-Ala-D-Ala-D-Arg) | Deltapak column 10–30% (80 min.) |
| 62 | D-Arg(Pmc)-D-Ala-D-Arg(Pmc)-MeIle-Leu | 25 | c(MeIle-Leu-Asp-Val-D-Arg-D-Ala-D-Arg) | 10–30% (60 min.) |

TABLE 1-continued

Synthesis and purification of cyclic peptides.

| NO: | Precursor | NO: | End Product Cyclic Peptide | High Pressure Liquid Chromatography (HPLC) (Gradient system and time) |
|---|---|---|---|---|
| 63 | Asp(OBut)-Val | | | |
| | D-Ala-D-Arg(Pmc)-D-Arg(Pmc)-MeIle-Leu-Asp(OBut)-Val | 26 | c(MeIle-Leu-Asp-Val-D-Ala-D-Arg-D-Arg) | 10–30% (60 min.) |
| 64 | D-Ala-D-Arg(Pbf)-D-Arg(Pbf)-MePhe-Leu-Asp(OBut)-Val | 27 | c(MePhe-Leu-Asp-Val-D-Ala-D-Arg-D-Arg) | 10–35% (60 min.) |
| 65 | D-Arg(Pbf)-D-Arg(Pbf)-D-Ala-MeIle-Leu-Asp(OBut)-Val | 28 | c(MeIle-Leu-Asp-Val-D-Arg-D-Arg-D-Ala) | 10–30% (60 min.) |
| 66 | D-Arg(Pbf)-D-Arg(Pbf)-D-Ala-MePhe-Leu-Asp(OBut)-Val | 29 | c(MePhe-Leu-Asp-Val-D-Arg-D-Arg-D-Ala) | 10–35% (60 min.) |
| 67 | D-Ala-D-Ala-D-Arg(Pmc)-D-Arg(Pmc)-MeIle-Leu-Asp(OBut)-Val | 30 | c(MeIle-Leu-Asp-Val-D-Ala-D-Ala-D-Arg-D-Arg) | 10–25% (60 min.) |
| 68 | D-Ala-D-Ala-D-Arg(Pmc)-D-Arg(Pmc)-MePhe-Leu-Asp(OBut)-Val | 31 | c(MePhe-Leu-Asp-Val-D-Ala-D-Ala-D-Arg-D-Arg) | 10–40% (60 min.) |
| 69 | Arg(Pbf)-D-Arg(Pbf)-D-Ala-D-Ala-D-MeIle-Leu-Asp(OBut)-Val | 32 | c(MeIle-Leu-Asp-Val-D-Arg-D-Arg-D-Ala-D-Ala) | 4" Vydac column 15–35% (100 min.) |
| 70 | D-Arg(Pmc)-MeIle-Leu-Asp(OBut)-Val-NH(CH$_2$)$_5$COOH | 33 | c(D-Arg-MeIle-Leu-Asp-Val-NH(CH$_2$)$_5$CO) | Deltapak column 15–30% (80 min.) |
| 71 | D-Arg(Pmc)-MeIle-Leu-Asp(OBut)-Val-NH(CH$_2$)$_2$—S—(CH$_2$)$_2$-COOH | 34 CO) | c(D-Arg-MeIle-Leu-Asp-Val-NH(CH$_2$)$_2$—S—(CH$_2$)$_2$— 15–30% (80 min.) | Deltapak column |
| 72 | D-Arg(Pmc)-MeIle-Leu-Asp(OBut)-Val-NH(CH$_2$)$_2$—S—CH$_2$-COOH | 35 CO) | c(D-Arg-MeIle-Leu-Asp-Val-NH(CH$_2$)$_2$—S—CH$_2$— 10–30% (80 min.) | Deltapak column |
| 73 | D-Arg(Pmc)-NH(CH$_2$)$_2$—S—CH$_2$CO-MeIle-Leu-Asp(OBut)-Val | 36 | c(MeIle-Leu-Asp-Val-D-Arg-NH(CH$_2$)$_2$—S—CH$_2$CO) | 10–40% (60 min.) |
| 74 | NH$_2$—CH$_2$—CH$_2$—S—CH$_2$—CO-D-Arg(Pmc)-D-Arg(Pmc)-MeIle-Leu-Asp(OBut)-Val | 37 | c(MeIle-Leu-Asp-Val-NH—CH$_2$—CH$_2$—S—CH$_2$—CO-D-Arg-D-Arg) | 10–40% (60 min.) |
| 75 | NH$_2$—CH$_2$—CH$_2$—S—CH$_2$—CO-D-Arg(Pmc)-D-Arg(Pmc)-MePhe-Leu-Asp(OBut)-Val | 38 | c(MePhe-Leu-Asp-Val-NH—CH$_2$—CH$_2$—S—CH$_2$—CO-D-Arg-D-Arg) | 10–30% (60 min.) |

Preparative HPLC was carried out using a reverse phase (C$_{18}$) 1 inch diameter Vydac column (218TP1022, 22 × 250 mm). In some cases (mentioned in the table) either a Deltapak column (30 × 300 mm) or a Vydac 4" column was used. The solvent system consisted of water and acetonitrile (each containing 0.1% trifluoroacetic acid). The column was eluted using a gradient (solvent ratio and time shown in the table) with increasing concentrations of acetonitrile run at a rate of 10 ml/minute for the Vydac column, 30 ml/min. for the Deltapak column and 100 ml/min. for the 4" Vydac column.

TABLE 2

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy (M + H)+ |
|---|---|---|---|---|
| 1 | 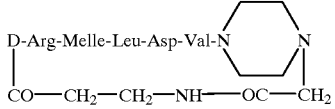 D-Arg-MeIle-Leu-Asp-Val-N⟨ ⟩N \| \| CO—CH₂—CH₂—NH—OC—CH₂ | Asp 1.0, Val 0.96, Leu 1.04, β-Ala 0.96, Arg 1.04 | 18.91 10–40% (30 min.) | 808.5 |
| 2 | 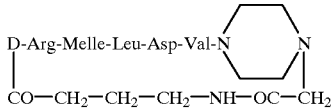 D-Arg-MeIle-Leu-Asp-Val-N⟨ ⟩N \| \| CO—CH₂—CH₂—CH₂—NH—OC—CH₂ | Asp 1.02, Val 0.96, Leu 1.04, γ-Abu 0.95, Arg 0.99 | 19.41 10–40% (30 min.) | 822.5 |
| 3 | c(MeIle-Leu-Asp-Val-D-Orn(CHMe₂)-D-Orn(CHMe₂)) | Asp 0.99, Val 0.97, Leu 1.04, Orn 2.01. | 23.45 10–40% (30 min.) | 767.5 |
| 4 | c(MeIle-Leu-Asp-Val-D-Lys(CHMe₂)-D-Ala) | Asp 1.0, Ala 1.0, Val 0.96, Leu 0.97. | 13.21 20–80% (40 min.) | 696.5 |
| 5 | c(MeIle-Leu-Asp-Val-D-Orn(Me₂)-D-Orn(Me₂)) | Asp 0.96, Val 1.02, Leu 1.02. | 25.82 10–60% (30 min.) | 740 |
| 6 | c(MeIle-Leu-Asp-Val-D-Ala-D-hArg(Et)₂) | Asp 1.0, Ala 1.06, Val 0.95, Leu 0.99, hArg(Et)₂, 0.97. | 13.34 20–80% (40 min.) | 752.4 |
| 7 | c(MeIle-Leu-Asp-Val-D-Phe-D-hArg(Et)₂) | Asp 1.0, Phe 0.96, Val 0.95, Leu 0.99, hArg(Et)₂, 0.98. | 16.49 20–80% (40 min.) | 828.9 |
| 8 | c(MeIle-Leu-Asp-Val-D-hArg(Et)₂-D-hArg(Et)₂) | Asp 1.0, Val 0.97, Leu 0.98, hArg(Et)₂, 2.1. | 12.03 20–80% (40 min.) | 907.6 |
| 9 | c(MeIle-Leu-Asp-Val-D-Lys-D-His) | Asp 1.02, Val 1.0, Leu 1.02, Lys 0.95, His 0.97. | 25.97 10–30% (40 min.) | 720.5 |
| 10 | c(MeIle-Leu-Asp-Val-D-Arg(Pmc)-D-Lys) | Asp 1.05, Val 1.0, Leu 0.99, Lys 0.99, Arg 0.95. | | 1005.5 |
| 11 | c(MeIle-Leu-Asp-Val-D-Lys-D-Arg) | Asp 1.05, Val 1.0, Leu 1.01, Lys 0.95, Arg 0.99. | 8.98 20–80% (40 min.) | 739.5 |
| 12 | c(MePhe-Leu-Asp-Val-D-Ala-D-Lys) | Asp 0.96, Ala 1.0, Val 0.95, Leu 1.05, Lys 0.95. | 24.27 10–40% (40 min.) | 688.2 |
| 13 | c(MeIle-Leu-Asp-Val-D-Arg-D-Lys) | Asp 1.05, Val 1.0, Leu 1.01, Lys 1.01, Arg 0.96. | 19.37 10–40% (40 min.) | 739.5 |
| 14 | c(Lys-Leu-Asp-Val-D-Ala-D-Ala) | Asp 1.0, Ala 2.09, Val 0.96, Leu 0.96, Lys 0.97. | 9.11 10–40% (40 min.) | 598.3 |
| 15 | c(Arg-Leu-Asp-Val-D-Ala-D-Ala) | Asp 1.0, Ala 2.06, Val 0.97, Leu 0.95, Arg 0.95. | 11.84 10–30% (40 min.) | 626.4 |
| 16 | c(D-Phe-Leu-Asp-Val-D-Ala-D-Lys) | Asp 1.0, Ala 1.05, Val 0.97, Leu 0.97, Lys 0.96, Phe 0.99. | 18.58 10–40% (40 min.) | 674.5 |
| 17 | c(MePhe-Leu-Asp-Val-D-Ala-D-Ala) | Asp 1.0, Ala 2.09, Val 0.97, Leu 0.98. | 16.92 20–80% (40 min.) | 631.4 |
| 18 | c(D-Phe-Leu-Asp-Val-D-Ala-D-Ala) | Asp 1.05, Ala 1.95, Val 1.0, Leu 0.98, Phe 0.95. | 12.34 20–80% (40 min.) | (M − H)⁻ 615.3 |
| 19 | c(D-Met-Leu-Asp-Val-D-Ala-D-Lys) | Asp 1.05, Ala 1.0, Val 1.01, Leu 1.03, Lys 1.03, Met 0.98. | 13.23 10–40% (40 min.) | 658.3 |
| 20 | c(MePhe-Leu-Asp-Val-D-Arg-D-Arg) | Asp 1.00, Val 0.96, Leu 1.0, Arg 1.96. | 21.19 10–40% (30 min.) | 801.4 |
| 21 | c(MePhe-Leu-Asp-Val-D-Arg-D-His) | Asp 1.03, Val 1.01, Leu 1.0, Arg 1.0, His 0.99. | 10.59 20–35% (15 min.) | 782.3 |
| 22 | c(MePhe-Leu-Asp-Val-D-Trp-D-Arg) | Asp 0.99, Val 0.97, Leu 1.0, Arg 1.03, Trp 0.59. | 7.89 30–45% (15 min.) | 831.0 |
| 23 | c(MePhe-Leu-Asp-Val-D-Arg-D-Ala-D-Arg) | Asp 1.04, Ala 1.05, Val 1.0, Leu 0.98, Arg 1.99. | 20.24 10–40% (40 min.) | 872.6 |
| 24 | c(MeIle-Leu-Asp-Val-D-Ala-D-Ala-D-Arg) | Asp 0.98, Ala 2.03, Val 0.97, Leu 1.0, Arg 1.01 | 21.19 10–40% (30 min.) | 753.4 |
| 25 | c(MeIle-Leu-Asp-Val-D-Arg-D-Ala-D-Arg) | Asp 1.04, Ala 0.98, Val 1.0, Leu 1.0, Arg 2.01 | 18.41 10–40% (40 min.) | 838.4 |
| 26 | c(MeIle-Leu-Asp-Val-D-Ala-D-Arg-D-Arg) | Asp 1.01, Ala 1.07, Val 1.0, Leu 1.0, Arg 1.90 | 23.68 10–40% (40 min.) | 838.5 |
| 27 | c(MePhe-Leu-Asp-Val-D-Ala-D-Arg-D-Arg) | Asp 1.05, Ala 1.0, Val 0.97, Leu 0.98, Arg 2.0 | 26.48 10–40% (40 min.) | 871.5 |
| 28 | c(MeIle-Leu-Asp-Val-D-Arg-D-Arg-D-Ala) | Asp 1.03, Ala 0.99, Val 1.0, Leu 1.0, Arg 1.97. | 23.16 10–30% (30 min.) | 838.4 |
| 29 | c(MePhe-Leu-Asp-Val-D-Arg-D-Arg-D-Ala) | Asp 1.02, Ala 1.0, Val 0.98, Leu 0.99, Arg 1.96. | 27.38 10–40% (30 min.) | 872.5 |
| 30 | c(MeIle-Leu-Asp-Val-D-Ala-D-Ala-D-Arg-D-Arg) | Asp 1.03, Ala 1.98, Val 0.97, Leu 1.0, Arg 2.05. | 22.55 10–40% (30 min.) | 909.6 |
| 31 | c(MePhe-Leu-Asp-Val-D-Ala-D-Ala-D-Arg-D-Arg) | Asp 1.06, Ala 2.09, Val 1.0, Leu 1.0, Arg 1.99 | 24.35 10–40% (30 min.) | 943.5 |

TABLE 2-continued

Synthesis and Characterisation of the Cyclic Peptides

| Comp. No. | End Product Cyclic Peptide | Amino Acid Analysis (Acid hydrolysis - 6N HCl containing 1% phenol, 24 hours, 130° C.) | HPLC Retention Time (Min.) | Mass Spectroscopy $(M + H)^+$ |
|---|---|---|---|---|
| 32 | c(MeIle-Leu-Asp-Val-D-Arg-D-Arg-D-Ala-D-Ala) | Asp 1.0, Ala 2.08, Val 0.96, Leu 1.05, Arg 1.95. | 24.33 10–40% (30 min.) | 909.5 |
| 33 | c(D-Arg-MeIle-Leu-Asp-Val-NH(CH$_2$)$_5$CO) | Asp 1.01, Val 0.98, Leu 0.99, Ahx 0.99, Arg 1.02 | 23.16 10–40% (30 min.) | 724.3 |
| 34 | c(D-Arg-MeIle-Leu-Asp-Val-NH(CH$_2$)$_2$—S—(CH$_2$)$_2$—CO) | Asp 1.03, Val 0.96, Leu 0.99, Arg 1.02 | 23.23 10–40% (30 min.) | 742 |
| 35 | c(D-Arg-MeIle-Leu-Asp-Val-NH(CH$_2$)$_2$—S—CH$_2$—CO) | Asp 0.97, Val 0.97, Leu 1.01, Arg 1.05 | 23.23 10–40% (30 min.) | 728.4 |
| 36 | c(MeIle-Leu-Asp-Val-D-Arg-NH(CH$_2$)$_2$—S—CH$_2$CO) | Asp 1.0, Val 1.02, Leu 1.04, Arg 1.01. | 17.37 20–40% (40 min.) | 728.4 |
| 37 | c(MeIle-Leu-Asp-Val-NH—CH$_2$—CH$_2$—S—CH$_2$—CO-D-Arg-D-Arg) | Asp 1.0, Val 1.0, Leu 1.01, Arg 2.0. | 13.0 20–40% (40 min.) | 884.4 |
| 38 | c(MePhe-Leu-Asp-Val-NH—CH$_2$—CH$_2$—S—CH$_2$—CO-D-Arg-D-Arg) | Asp 1.0, Val 0.95, Leu 0.98, Arg 1.97. | 16.0 20–40% (40 min.) | 918.4 |

Analytical HPLC was carried out using either a reverse phase (C$_{18}$) Vydac column (218TP54, 4.6 × 250 mm) or a Novapak column (3.9 × 150 mm). Unless otherwise stated in the above table a Vydac column was used for the compound. The solvent system consisted of water and acetonitrile (each containing 0.1% trifluoroacetic acid). The column was eluted using a gradient (solvent ratio and time shown in the table) with increasing concentrations of acetonitrile run at a rate of 1 ml/minute. The presence of some of the unnatural amino acids was observed in the amino acid analysis but the quantities were not estimated.

What is claimed is:

1. A cyclic peptide of the formula

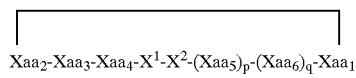

Xaa$_2$-Xaa$_3$-Xaa$_4$-X$^1$-X$^2$-(Xaa$_5$)$_p$-(Xaa$_6$)$_q$-Xaa$_1$ where

Xaa$_1$ is selected from an L-amino acid or a D-amino acid, wherein the L-amino acid is selected from Phe, Lys and Arg, the D-amino acid is selected from Phe and Met, and the L- or D-amino acid optionally is substituted on its ax-carbon or ax-amino group with a C$_{1-4}$ alkyl group, or Xaa$_1$ is MeIle;

Xaa$_2$ is Leu, optionally substituted on its α-carbon or α-amino group with a C$_{1-4}$ alkyl group;

Xaa$_3$ is Asp, optionally substituted on its α-carbon or cc-amino group with a C$_{1-4}$ alkyl group;

Xaa$_4$ is Val, optionally substituted on its α-carbon or α-amino group with a C$_{1-4}$ alkyl group;

X$^1$ is a D-amino acid selected from Ala, Phe, Arg, Lys, Trp, hArg(Et)$_2$, Orn(CHMe$_2$), Orn(Me$_2$), Lys(CHMe$_2$) and Arg(Pmc), optionally substituted on its α-carbon or its α-amino group with a C$_{1-4}$ alkyl group;

or

X$^1$ is

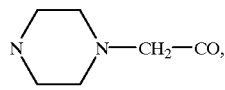

NH(CH$_2$)$_5$CO, or NH(CH$_2$)$_2$S(CH$_2$)$_y$CO where y is 1 or 2;

X$^2$ is a D-amino acid selected from Ala, Arg, Lys, His, hArg(Et)$_2$, Orn(CHMe$_2$), and Orn(Me$_2$), optionally substituted on its α-carbon or its α-amino group with a C$_{1-4}$ alkyl group, or x$^2$ is NH(CH$_2$)$_2$SCH$_2$CO, or NH(CH$_2$)$_x$CO where x is 2 or 3;

Xaa$_5$ and Xaa$_6$ are each, independently, a D-amino acid selected from Ala and Arg, optionally substituted on its α-carbon or α-amino group with a C$_{1-4}$ alkyl group;

p is 0 or 1; and q is 0 or when p is 1, q is 0 or 1;

or a salt thereof;

with the proviso that when Xaa$_1$ is MeIle, Xaa$_2$ is Leu, Xaa$_3$ is Asp, Xaa$_4$ is Val and p and q are both 0, then i) X$^2$ is not D-Ala, D-Arg, or D-Lys when X$^1$ is D-Ala;

ii) X$^2$ is not D-Arg when X$^1$ is

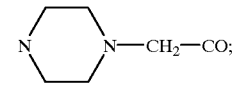

iii) X$^2$ is not D-Ala, D-Arg or D-His when X$^1$ is D-Arg;

iv) X$^2$ is not D-Ala when X$^1$ is D-Orn(CHMe$_2$) or D-Arg(Pmc);

v) x$^2$ is not D-Ala or D-Lys when X$^1$ is D-Lys; and vi) X$^2$ is not D-Lys or D-Arg when X$^1$ is D-Phe or D-Trp.

2. A cyclic peptide according to claim 1 where

Xaa$_1$ is an L-amino acid selected from Meae, MePhe, Lys and Arg, or a D-amino acid selected from Phe and Met;

Xaa$_2$, Xaa$_3$ and Xaa$_4$ are, respectively, Leu, Asp, and Val;

X$^1$ is a D-amino acid selected from Ala, Phe, Arg, Lys, Trp, hArg(Et)$_2$, Orn(CHMe$_2$), Orn(Me$_2$), Lys(CHMe$_2$) and Arg(Pmc), or X¹ is

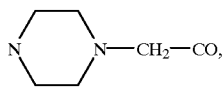

NH(CH$_2$)$_5$CO, or NH(CH$_2$)$_2$S(CH$_2$)$_y$CO where y is 1 or 2;

X² is a D-amino acid selected from Ala, Arg, Lys, His, hArg(Et)$_2$, Orn(CHMe$_2$), and Orn(Me$_2$), or X² is NH(CH$_2$)$_2$SCH$_2$CO, or NH(CH$_2$)$_x$CO where x is 2 or 3;

Xaa$_5$ and Xaa$_6$ are each, independently, a D-amino acid selected from Ala and Arg;

or a salt thereof.

3. A cyclic peptide of the formula

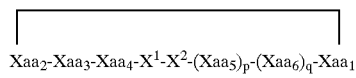

where

Xaa$_1$ is an L-amino acid selected from Phe, Lys and Arg, a D-amino acid selected from Phe and Met, and the L- or D-amino acid optionally is substituted on its α-carbon or its α-amino group with a C$_{1-4}$ alkyl group, or Xaa$_1$ is MeIle;

Xaa$_2$ is Leu, optionally substituted on its α-carbon or α-amino group with a C$_{1-4}$ alkyl group;

Xaa$_3$ is Asp, optionally substituted on its α-carbon or α-amino group with a C$_{1-4}$ alkyl group;

Xaa$_4$ is Val, optionally substituted on its α-carbon or α-amino group with a C$_{1-4}$ alkyl group;

X¹ is a D-amino acid selected from Ala, Phe, Arg, Lys, Trp, hArg(Et)$_2$, Orn(CHMe$_2$), Orn(Me$_2$), Lys(CHMe$_2$) and Arg(Pmc), optionally substituted on its α-carbon or its α-amino group with a C$_{1-4}$ alkyl group, or X¹ is

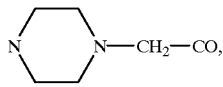

NH(CH$_2$)$_5$CO, or NH(CH$_2$)$_2$S(CH$_2$)$_y$CO where y is 1 or 2;

X² is a D-amino acid selected from Ala, Arg, Lys, His, hArg(Et)$_2$, Orn(CHMe$_2$), and Orn(Me$_2$), optionally substituted on its oα-carbon or its α-amino group with a C$_{1-4}$ alkyl group, or X² is NH(CH$_2$)$_2$SCH$_2$CO, or NH(CH$_2$)$_x$CO where x is 2 or 3;

Xaa$_5$ and Xaa$_6$ are each, independently, a D-amino acid selected from Ala and Arg, optionally substituted on its α-carbon or α-amino group with a C$_{1-4}$ alkyl group;

is 0 or 1; and q is 0 or when p is 1, q is 0 or 1;

or a salt thereof, with the proviso that when p and q are both 0, Xaa$_1$ is not MeIle.

4. A cyclic peptide of the formula

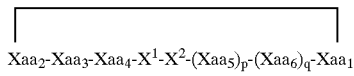

where

Xaa$_1$ is a L-amino acid selected from MePhe and MeIle;

Xaa$_2$ is Leu, optionally substituted on its α-carbon or α-amino group with a C$_{1-4}$ alkyl group;

Xaa$_3$ is Asp, optionally substituted on its α-carbon or α-amino group with a C$_{1-4}$ alkyl group;

Xaa$_4$ is Val, optionally substituted on its α-carbon or α-amino group with a C$_{1-4}$ alkyl group;

X¹ is a D-amino acid selected from Ala and Arg, optionally substituted on its α-carbon or its α-amino group with a C$_{1-4}$ alkyl group;

or

X¹ is

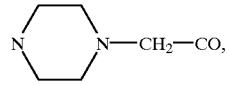

or NH(CH$_2$)$_2$S(CH$_2$)$_y$CO where y is 1 or 2;

X² is a D-amino acid selected from Ala and Arg, optionally substituted on its α-carbon or its α-amino group with a C$_{1-4}$ alkyl group, or X² NH(CH$_2$)$_x$CO where x is 2 or 3;

Xaa$_5$ and Xaa$_6$ are each, independently, a D-amino acid selected from Ala and Arg, optionally substituted on its α-carbon or α-amino group with a C$_{1-4}$ alkyl group;

p is 1; and q is 0 or 1;

or a salt thereof.

5. A cyclic peptide according to claim 1 where any two of X¹, X², (Xaa$_5$)$_p$ and (Xaa$_6$)$_q$ are D-Arg or a salt thereof.

6. A cyclic peptide according to claim 3 where Xaa$_1$ is MePhe.

7. A cyclic peptide according to claim 4 where p is 1 and q is 1; or a salt thereof.

8. A cyclic peptide according to claim 4 where p is 1 and q is 0; or a salt thereof.

9. A cyclic peptide according to claim 1 where the cyclic peptide is selected from

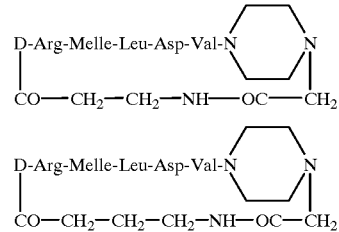

c(MeIle-Leu-Asp-Val-D-Orn(CHMe$_2$)-D-Orn(CHMe$_2$))
c(MeIle-Leu-Asp-Val-D-Lys(CIHMe$_2$)-D-Ala)
c(MeIle-Leu-Asp-Val-D-Orn(Me$_2$)-D-Orn(Me$_2$))
c(MeIle-Leu-Asp-Val-D-Ala-D-hArg(Et)$_2$)
c(MeIle-Leu-Asp-Val-D-Phe-D-hArg(Et)$_2$)
c(MeIle-Leu-Asp-Val-D-hArg(Et)$_2$-D-hArg(Et)$_2$)

c(MeIle-Leu-Asp-Val-D-Lys-D-His)
c(MeIle-Leu-Asp-Val-D-Arg(Pmc)-D-Lys)
c(MeIle-Leu-Asp-Val-D-Lys-D-Arg)
c(MePhe-Leu-Asp-Val-D-Ala-D-Lys)
c(MeIle-Leu-Asp-Val-D-Arg-D-Lys)
c(Lys-Leu-Asp-Val-D-Ala-D-Ala)
c(Arg-Leu-AspVal-D-Ala-D-Ala)
c(D-Phe-Leu-Asp-Val-D-Ala-D-Lys)
c(MePhe-Leu-Asp-Val-D-Ala-D-Ala)
c(D-Phe-Leu-Asp-Val-D-Ala-D-Lys)
c(D-Met-Leu-Asp-Val-D-Ala-D-Lys)
c(MePhe-Leu-Asp-Val-D-Arg-D-Arg)
c(MePhe-Leu-Asp-Val-D-Arg-D-His)
c(MePhe-Leu-Asp-Val-D-Trp-D-Arg)
c(MePhe-Leu-Asp-Val-D-Arg-D-Ala-D-Arg)
c(MeIle-Leu-Asp-Val-D-Ala-D-Ala-D-Arg)
c(MeIle-Leu-Asp-Val-D-Arg-D-Ala-D-Arg)
c(MeIle-Leu-Asp-Val-D-Ala-D-Arg-D-Arg)
c(MePhe-Leu-Asp-Val-D-Ala-D-Arg-D-Arg)
c(MeIhe-Leu-Asp-Val-D-Arg-D-Arg-D-Ala)
c(MePhe-Leu-Asp-Val-D-Arg-D-Arg-D-Ala)
c(MeIhe-Leu-Asp-Val-D-Ala-D-Ala-D-Arg-D-Arg)
c(MePhe-Leu-Asp-Val-D-Ala-D-Ala-D-Arg-D-Arg)
c(MeIle-Leu-Asp-Val-D-Arg-D-Arg-D-Ala-D-Ala)
c(D-Arg-MeIle-Leu-Asp-Val-NH(CH$_2$)$_5$CO)
c(D-Arg-MeIle-Leu-Asp-Val-NH(CH$_2$)$_2$—S—(CH$_2$)$_2$—CO)
c(D-Arg-MeIle-Leu-Asp-Val-NH(CH$_2$)$_2$—S—CH$_2$—CO)
c(MeIle-Leu-Asp-Val-D-Arg-NH(CH$_2$)$_2$—S—CH$_2$—CO)
c(MeIle-Leu-Asp-Val-NH-CH$_2$—CH$_2$—S—CH$_2$—CO-D-Arg-D-Arg), and
c(MePhe-Leu-Asp-Val-NH-CH$_2$—CH$_2$—S—CH$_2$—CO-D-Arg-D-Arg).

10. A cyclic peptide according to claim 9 selected from
c(MeIle-Leu-Asp-Val-D-hArg(Et)$_2$-D-hArg(Et)$_2$)
c(MePhe-Leu-Asp-Val-D-Arg-D-Arg)
c(MePhe-Leu-Asp-Val-D-Arg-D-His)
c(MePhe-Leu-Asp-Val-D-Trp-D-Arg)
c(MePhe-Leu-Asp-Val-D-Arg-D-Ala-D-Arg)
c(MeIle-Leu-Asp-Val-D-Arg-D-Ala-D-Arg)
c(MeIle-Leu-Asp-Val-D-Ala-D-Arg-D-Arg)
c(MePhe-Leu-Asp-Val-D-Ala-D-Arg--D-Arg)
c(MeIle-Leu-Asp-Val-D-Arg-D-Arg-D-Ala)
c(MePhe-Leu-Asp-Val-D-Arg-D-Arg-D-Ala)
c(MeIle-Leu-Asp-Val-D-Ala-D-Ala-D-Arg-D-Arg)
c(MePhe-Leu-Asp-Val-D-Ala-D-Ala-D-Arg-D-Arg)
c(MeIle-Leu-Asp-Val-D-Arg-D-Arg-D-Ala-D-Ala)
c(MeIle-Leu-Asp-Val-NH-CH$_2$—CH$_2$—S—CH$_2$—CO-D-Arg-D-Arg), and
c(MePhe-Leu-Asp-Val-NH-CH$_2$—CH$_2$—S—CH$_2$—CO-D-Arg-D-Arg).

11. A cyclic peptide according to claim 10 of formula c(MePhe-Leu-Asp-Val-D-Arg-D-His).

12. A cyclic peptide according to claim 10 of formula c(MePhe-Leu-Asp-Val-D-Arg-D-Arg).

13. A cyclic peptide according to claim 10 of formula c(MePhe-Leu-Asp-Val-D-Ala-D-Arg-D-Arg).

14. A cyclic peptide according to claim 10 of formula c(MePhe-Leu-Asp-Val-D-Ala-D-Ala-D-Arg-D-Arg).

15. A pharmaceutical composition comprising a cyclic peptide according to any one of claims 1, 2, 5, 3, 6, 4 and 7 to 14, or and 7 to 14, or a pharmaceutically acceptable salt thereof in association with a pharmaceutically acceptable diluent or carrier.

16. A method for inhibiting the interaction between VCAM-1 and/or fibronectin and the integrin receptor VLA-4 in mammals in need of such treatment which comprises administering to said mammal an effective amount of a cyclic peptide according to any one of claims 1, 2, 5, 3, 6, 4 and 7 to 14, or a pharmaceutically acceptable salt thereof.

17. The method according to claim 16 for treating multiple sclerosis, rheumatoid arthritis, asthma or psoriasis.

18. A method for inhibiting the interaction between MAdCAM-1 and the integrin α4β7 in mammals in need of such treatment which comprises administering to said mammal an effective amount of a cyclic peptide according to any one of claims 1, 2, 5, 3, 6, 4 and 7 to 14, or a pharmaceutically acceptable salt thereof.

19. A process for the manufacture of a cyclic peptide or a salt thereof as claimed in any of claims 1, 2, 5, 3, 4, and 7 to 14, selected from process routes (a), (b) and (c):

(a) assembling the required linear peptide in a stepwise manner (adding one amino acid at a time) followed by selective removal of any N- and C-terminal protecting groups, cyclisation and finally deprotonation to give said cyclic peptide, and optionally converting said cyclic peptide into a salt thereof;

(b) forming an amide bond by coupling two peptide units, one containing a carboxylic acid group, or a reactive derivative thereof, and the other containing an amino group, such that said cyclic peptide in protected or unprotected form is produced, and removing any protecting group using process route (c) below, and optionally converting the product thus obtained into a salt thereof; and (c) removing one or more conventional peptide protecting groups from a protected cyclic peptide of formula

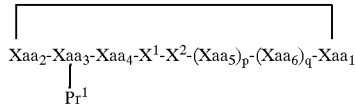

where Pr$^1$ is a protecting group on the acid group in the side of chain of Xaa$_3$ to give said cyclic peptide in protected or unprotected form, simultaneously or subsequently removing any additional conventional peptide protecting group present, and optionally converting the product thus obtained into a salt thereof.

* * * * *

UNITED STATES PATENT AND TRADEMARK OFFICE
CERTIFICATE OF CORRECTION

PATENT NO. : 6,235,711 B1 Page 1 of 1
DATED : May 22, 2001
INVENTOR(S) : Dutta

It is certified that error appears in the above-identified patent and that said Letters Patent is hereby corrected as shown below:

<u>Title page,</u>
Please change Item [22], to read:
-- [22] PCT Filed: 18 June 1997 --.

Please insert the following lines following Item [22]:

-- [86] PCT No.: PCT/GB97/01641

§ 371 Date: Dec. 21, 1998

§ 102(e) Date: Dec. 21, 1998

[87] PCT Pub. No.: WO 97/49731

PCT Pub. Date: Dec. 31, 1997 --

Signed and Sealed this

Fourth Day of November, 2003

JAMES E. ROGAN
*Director of the United States Patent and Trademark Office*